US009532748B2

(12) United States Patent
Denison et al.

(10) Patent No.: US 9,532,748 B2
(45) Date of Patent: Jan. 3, 2017

(54) METHODS AND DEVICES FOR BRAIN ACTIVITY MONITORING SUPPORTING MENTAL STATE DEVELOPMENT AND TRAINING

(71) Applicant: Personal Neuro Devices Inc., Ottawa (CA)

(72) Inventors: Steve Denison, Ottawa (CA); Andrew Stephen Faulkner, Ottawa (CA); Tony Gaitatzis, Walnut (CA); Arwen Moore, Ottawa (CA); Chad Veinotte, Ottawa (CA); Bruno Daoust, Ottawa (CA); Elliott Alfred Loh, Ottawa (CA)

(73) Assignee: Personal Neuro Devices Inc., Ottawa (CA)

( * ) Notice: Subject to any disclaimer, the term of this patent is extended or adjusted under 35 U.S.C. 154(b) by 182 days.

(21) Appl. No.: 14/258,282

(22) Filed: Apr. 22, 2014

(65) Prior Publication Data

US 2014/0316230 A1  Oct. 23, 2014

Related U.S. Application Data

(60) Provisional application No. 61/814,583, filed on Apr. 22, 2013.

(51) Int. Cl.
*A61B 5/0478* (2006.01)
*A61B 5/00* (2006.01)
(Continued)

(52) U.S. Cl.
CPC .......... *A61B 5/6803* (2013.01); *A61B 5/0006* (2013.01); *A61B 5/04012* (2013.01);
(Continued)

(58) Field of Classification Search
CPC .... A61B 5/0478; A61B 5/6803; A61B 5/6814
(Continued)

(56) References Cited

U.S. PATENT DOCUMENTS 3,659,614 A * 5/1972 Jankelson .............. A61N 1/321
607/139
5,495,853 A * 3/1996 Yasushi ................ A61B 5/0482
600/27
(Continued)

*Primary Examiner* — Lee S Cohen
(74) *Attorney, Agent, or Firm* — The Law Office of Michael E. Kondoudis

(57) ABSTRACT

With explosive penetration of portable electronic devices (PEDs) recent focus into consumer EEG devices has been to bring advantages including localized wireless interfacing, portability, and a low-cost high-performance electronics platform to host the processing algorithms to bear. However, most development continues to focus on brain-controlled video games which are nearly identical to those created for earlier, more stationary consumer EEG devices and personal EEG is treated as of a novelty or toy. According to embodiments of the invention the inventors have established new technologies and solutions that address these limitations within the prior art and provide benefits including, but not limited to, global acquisition and storage of acquired EEG data and processed EEG data, development interfaces for expansion and re-analysis of acquired EEG data, integration to other non-EEG derived user data, and long-term user wearability.

19 Claims, 13 Drawing Sheets

(51) Int. Cl.
*A61B 5/04* (2006.01)
*A61B 5/16* (2006.01)
*A61B 5/0482* (2006.01)

(52) U.S. Cl.
CPC .......... *A61B 5/0478* (2013.01); *A61B 5/0482* (2013.01); *A61B 5/165* (2013.01); *A61B 5/168* (2013.01); *A61B 5/4088* (2013.01); *A61B 5/4094* (2013.01); *A61B 5/4806* (2013.01); *A61B 5/7264* (2013.01); *A61B 5/742* (2013.01)

(58) Field of Classification Search
USPC ........................................................ 600/383
See application file for complete search history.

(56) References Cited

U.S. PATENT DOCUMENTS

| | | | | |
|---|---|---|---|---|
| 2007/0225585 | A1* | 9/2007 | Washbon | A61B 5/0478 600/393 |
| 2010/0217100 | A1* | 8/2010 | LeBoeuf | A61B 5/00 600/301 |
| 2013/0012802 | A1* | 1/2013 | Horseman | A61B 5/0476 600/383 |
| 2014/0249385 | A1* | 9/2014 | Wada | A61B 5/0478 600/301 |
| 2015/0374971 | A1* | 12/2015 | Dar | A61N 1/0484 607/139 |

\* cited by examiner

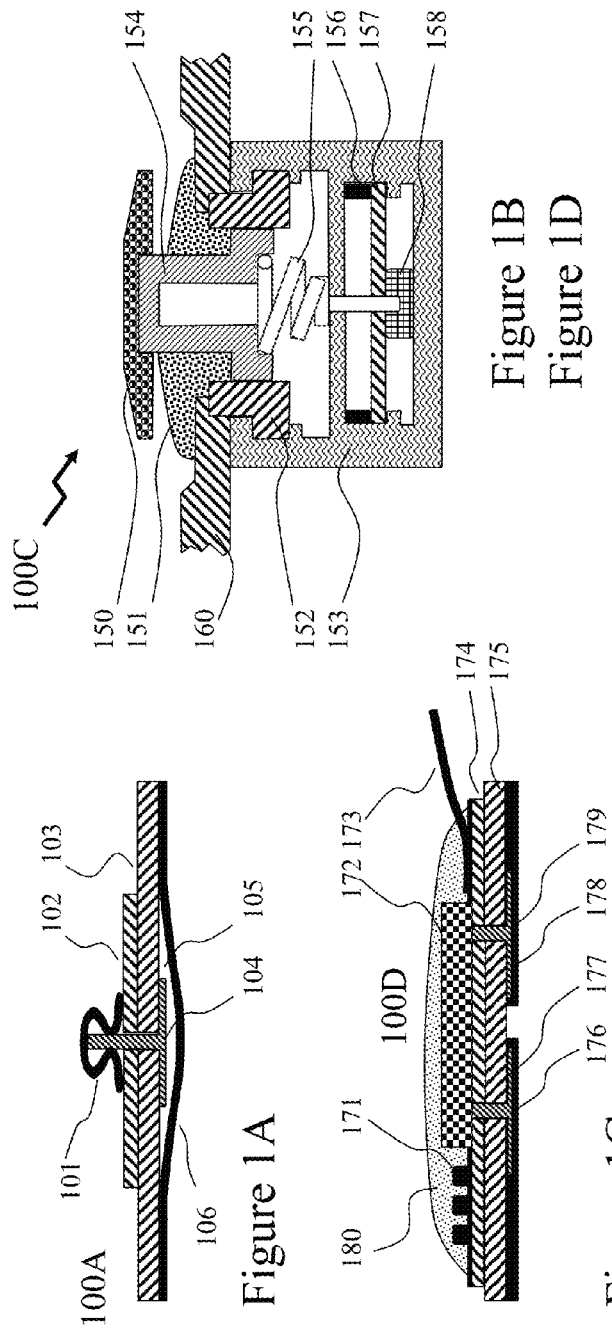
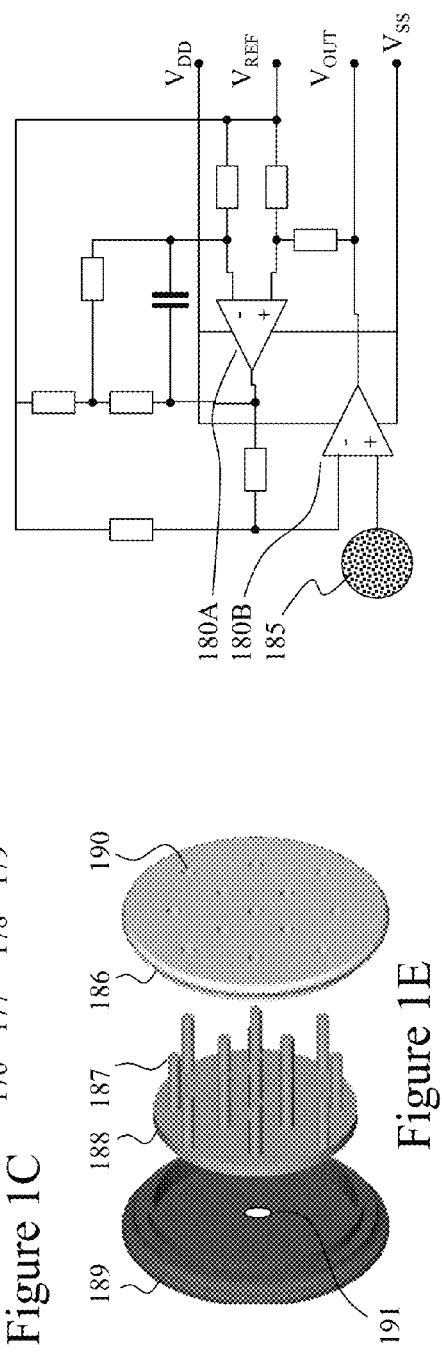
Figure 1A
Figure 1B
Figure 1C
Figure 1D
Figure 1E

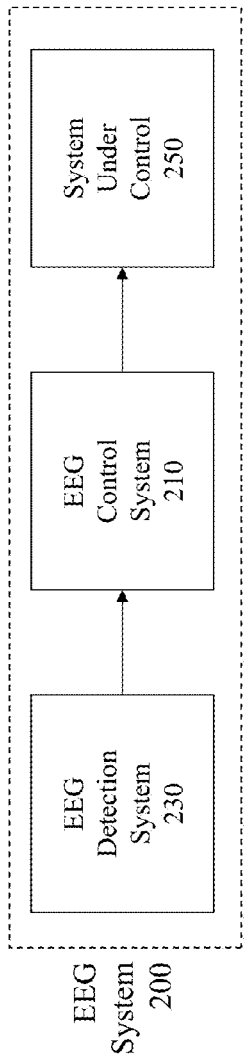
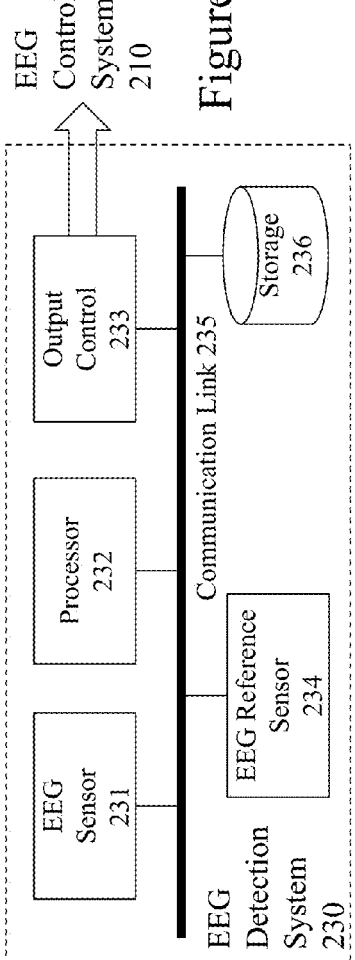
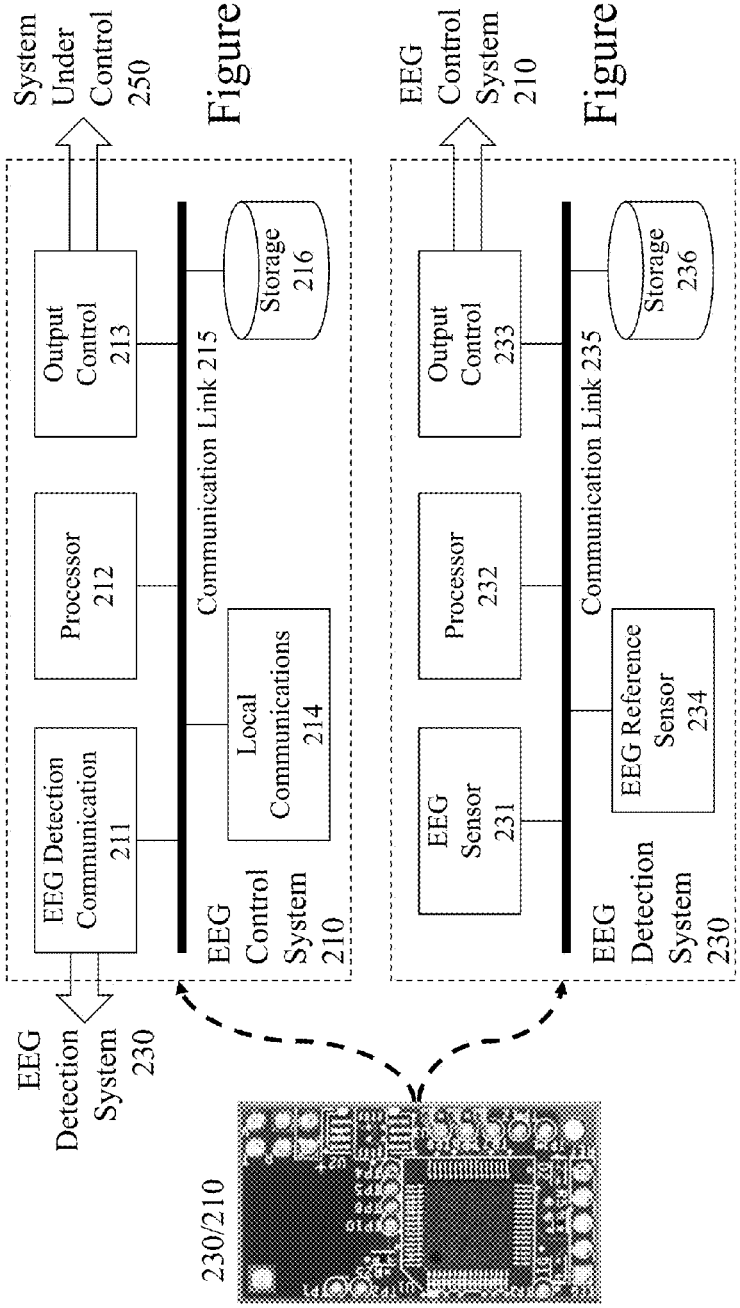
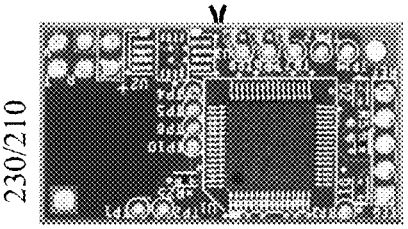

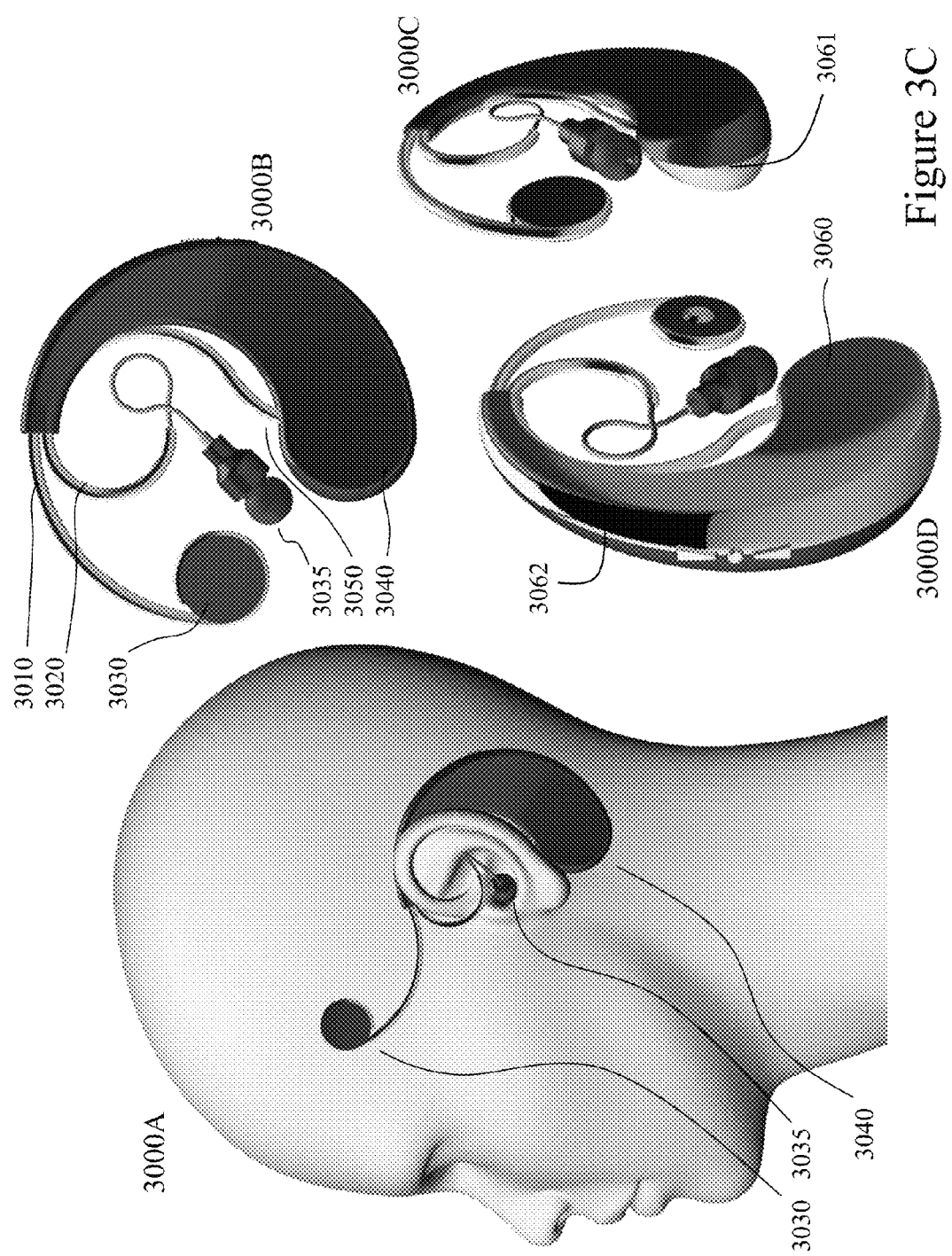

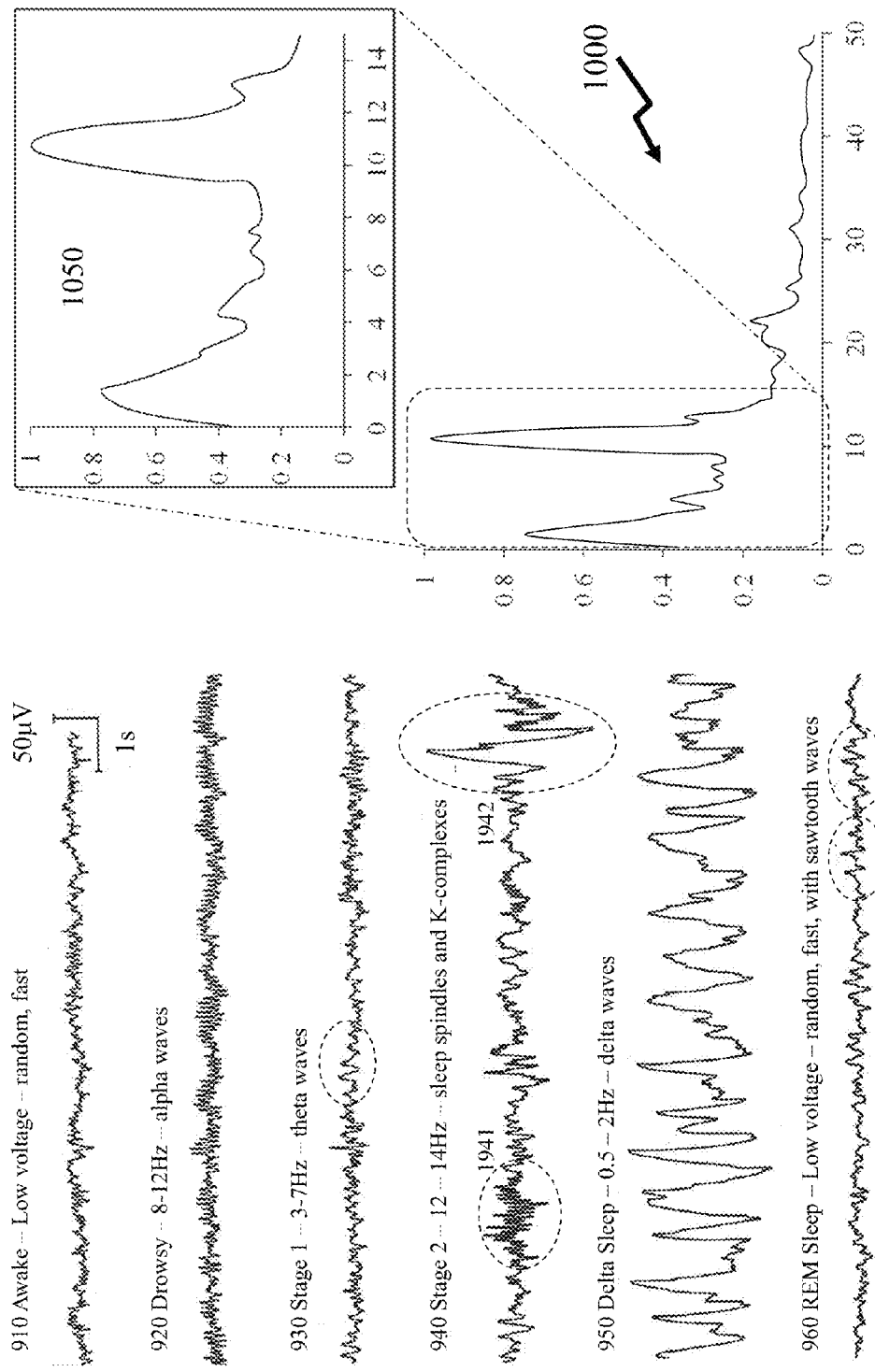

METHODS AND DEVICES FOR BRAIN ACTIVITY MONITORING SUPPORTING MENTAL STATE DEVELOPMENT AND TRAINING

CROSS-REFERENCE TO RELATED APPLICATIONS

This patent application claims the benefit of U.S. Provisional Patent Application 61/814,583 filed on Apr. 22, 2013 entitled "Methods and Devices for Brain Activity Monitoring Supporting Mental State Development and Training."

FIELD OF THE INVENTION

The present invention relates to EEG-based brain activity monitoring devices, and more particularly to portable systems for brain activity recording, storage, analysis, and neurofeedback that operate in conjunction with an application and web-based framework for more extensive storage and analysis.

BACKGROUND OF THE INVENTION

Brain Computer Interfaces (BCIs) are devices that allow the human brain to directly interact with technology via signals emitted from the skull. As with many such new technologies relating to the human brain and body, BCIs were first developed and used in laboratory, clinical, medical, and research settings. However, in recent years electroencephalography (EEG)-based BCI headsets have reached consumer-accessible prices, and are now being deployed in mobile applications, especially those focused on gaming and mental development. Medical applications of BCIs are beginning to include helping people with locked-in syndrome communicate; providing more autonomy to people with neuromuscular disorders; and helping with the rehabilitation of stroke survivors. Additionally, BCIs may aid in diagnosis and lead to preventative protocols for brain disorders, which are particularly important, in part due to increasing average life-expectancy, population growth, and number of people over the age of 65, i.e. Alzheimer's disease and other forms of age-related dementia are becoming an increasingly large problem. Furthermore, surveys consistently show that a large (and increasing) portion of the population suffers from some sort of mental illness: e.g. in 2010 approximately 1 in 3 Europeans met DSM-IV criteria for a mental or neurological disorder, see for example Wittchen et al. in "The Size and Burden of Mental Disorders and other Disorders of the Brain in Europe 2010" (European Neuropsychopharmacology, Vol. 21(9), pp. 655-679), in 2004 the rate was 1 in 4 in the United States, see for example Wittchen et al. in "Size and Burden of Mental Disorders in Europe—A Critical Review and Appraisal of 27 Studies" (European Neuropsychopharmacology, Vol. 15(4), pp 0.357-376).

Beyond medical applications, BCIs can provide members of the general public with insight into various aspects of their mental health, and act as tools for controlling/interacting with electronic systems. Additionally, EEG-based BCI devices can be used for neurofeedback, a series of techniques that give users the opportunity to train their brain by (among other things) increasing their ability to focus, reducing stress and anxiety levels, elevating mood, improving sleep, and enhancing cognitive processing and mental clarity. Also, neurofeedback can also be used as a treatment for a number of brain disorders, e.g. attention deficit hyperactivity disorder (ADHD), see for example Gevensleben et al. in "Is Neurofeedback an Efficacious Treatment for ADHD? A Randomised Controlled Clinical Trial." (J. Child Psychology and Psychiatry, Vol. 50(7), pp. 780-789), and epilepsy, see for example Kotchoubey et al. in "Negative Potential Shifts and the Prediction of the Outcome of Neurofeedback Therapy in Epilepsy (Clinical Neurophysiology, Vol. 110(4), pp. 683-6).

Current BCIs range in complexity from medical/research-grade EEG devices with hundreds of sensors, to small headphone-like plastic headsets with only one or two. EEG headsets are designed for numerous purposes, but they typically fall into 2 categories: 1) medical/research headsets with a large number of sensors; and 2) simple devices with a small number of electrodes geared towards consumer devices and applications: e.g. games and general health and wellness software. Typically, medical/research headsets are bulky, stationary, uncomfortable, complex, user-unfriendly (and can thus only be operated by technicians and medical professionals), unattractive, and often require electrolyte solutions, glues, or gels for connectivity. Accordingly, it is beneficial to design sensors/electrodes/user interfaces with these issues in mind, i.e. a BCI that supports use for durations considerably longer than those of discrete medical visits and laboratory studies, but that still exhibits many of the most useful features of currently existing consumer and especially medical/research BCI headsets.

Electroencephalography (EEG) is a well-established technology that gathers information about what's going on inside a person's brain by recording signals produced by the firing of their neurons. When a neuron receives enough excitatory signals from sensory cells and other neurons, it produces a response called an action potential, which causes the neuron to release chemicals that excite all cells connected to a part of the firing neuron called the axon. During this process, there is a rapid exchange of ions (electrically-charged particles) that changes the voltage of the fluid surrounding the firing neuron in a predictable fashion. This voltage change then travels spherically outward from the firing neuron until it reaches the skull. EEG takes advantage of this to record brain activity by detecting voltages at one or more scalp locations over time (which alter in response to the firing of many neurons simultaneously), using electrodes attached to the surface of the head. Voltages are sampled from the electrodes at high frequencies—typically 1 kHz to 2 kHz—to provide an effectively continuous stream of data known as an EEG waveform. Spectral information is then extracted from this continuous stream, which results in discrete frequency-band ratios (wave types) generated from the raw data at frequencies in the ballpark of 100 Hz; for example, see Tatum et al in "Handbook of EEG Interpretation" (Demos Medical Publishing, 2008). These are generally divided into delta, theta, alpha, beta, mu, and gamma waves, with each type representing a specific range of frequencies. Some systems further subdivide these waveforms into subcategories, such as alpha1, alpha2, etc.—which essentially subdivide the frequency range of the entire waveform into smaller frequency ranges.

Past research has shown that different EEG waveforms correlate with activity in different regions of the brain, and thus with various internal mental states, for example particular emotions and thoughts, phases of sleep such as REM, and medically relevant neurological activity (e.g. seizures). Specific mental states can be identified by mathematically pre-processing the raw EEG data (e.g. using Fourier transforms; with various filters such as high-pass filters, low-pass filters, and bandpass filters; etc.), then applying algorithms that recognize EEG waveform features associated with a particular state—known as classification algorithms; see for example Shaker in "EEG Waves Classifier using Wavelet Transform and Fourier Transform" (Int. J. Biol. Life. Sci., Vol. 1, Iss. 2, p85-90). Algorithms exist for the quantification and tracking of mood, energy levels, epileptic seizures and seizure-like states, stages and quality of sleep, desire or craving for a particular object (e.g. a specific food), blinks, concentration/focus, relaxation/stress, and anxiety; see for example Rebolledo-Mendez et al in "Assessing Neurosky's Usability to Detect Attention Levels in an Assessment Exercise: (Human and Computer Interaction, pp 149-158, Springer-Verlag, 2009); and Crowley et al in "Evaluating a Brain-Computer Interface to Categorise Human Emotional Response" (IEEE $10^{th}$ Int. Conf. Adv. Learning Technologies, pp 276-278). Accordingly, within the prior art EEG waveforms have been used to document a range of a user's neural processes and mental states.

This ability to externally read and record specific mental states led to neurofeedback: EEG-based treatments for neurological and/or mental disorders that use exercises developed to allow a person to alter these mental states directly (by manipulating its constituent waveforms). For example, knowledge of the EEG patterns correlated with attention—mainly beta waves—led to effective neurofeedback exercises for improving concentration, in which the feedback a user receives from the EEG analysis informs them of the extent to which they are focused. This allows users to purposefully induce these states by repeating the thought patterns they were engaged in when high levels of focus were reported by the EEG device. Increasing concentration in this manner actually strengthens the involved areas of the brain, such that the user sees improved focus in their day-to-day life, beyond the context of the exercise itself. This was demonstrated by research showing that 1) these areas of the brain observably grow, see for example Beauregard et al in "Functional Magnetic Resonance Imaging Investigation of the Effects of Neurofeedback Training on the Neural Bases of Selective Attention and Response Inhibition in Children with Attention-Deficit/Hyperactivity Disorder" (Appl. Psychophysiology and Biofeedback, Vol. 31, pp 3-20; and 2) it significantly improves symptoms of attention-deficit hyperactivity disorder (ADHD), a condition marked by a pathologically low attention span; see for example Arms et al in "Efficacy of Neurofeedback Treatment in ADHD: The Effects on Inattention, Impulsivity, and Hyperactivity: A Meta-Analysis" (Clinical EEG Neurosciences et al, Vol. 40(3), pp 180-189). This, however, is merely an example, as other research has demonstrated the efficacy of neurofeedback-related therapies for the treatment of conditions involving other mental states, such as depression using mood-elevating exercises and anxiety with neurofeedback-informed relaxation techniques, see for example Baehr et al in "Clinical Use of an Alpha Asymmetry Neurofeedback Protocol in the Treatment of Mood Disorders: Follow-Up Study One to Five Years Post Therapy" (J Neurotherapy, Vol. 4(4), pp 11-18) and Hammond in "Neurofeedback Treatment of Depression and Anxiety" (J Adult Dev., Vol. 12(2-3), pp 131-137).

Neurofeedback can also benefit people without mental or neurological disorders. Recent research has shown improvements in attention, semantic memory, and musical performance in healthy people after using neurofeedback exercises specifically designed to target each of those attributes. These performance enhancements were shown to translate into real-world settings; see for example Egner et al in "Ecological Validity of Neurofeedback: Modulation of Slow Wave EEG Enhances Musical Performance" (Neuroreport, Vol. 14, pp 1221-1224). Thus, neurofeedback can be used to cultivate desirable personal traits and improve quality of life, rather than simply to treat disorders. It is therefore a valuable tool for self-improvement that can allow healthy people to strengthen areas of cognitive and emotional weakness, and to improve their existing strengths.

Until recently, EEG measurement devices were expensive, bulky, stationary, and extremely difficult to use, and thus confined to a laboratory, clinic, or hospital setting. They were therefore only useful for research, diagnosis of various brain diseases, and for treatment of certain disorders in a clinical practice setting—which is very expensive. Accordingly, numerous potential treatments targeting neurological and mental disorders that require frequent, long-term, and self-administered EEG (IE a neurofeedback regiment that requires an extremely large number of sessions, which continue to be done intermittently near-indefinitely) were essentially impossible, as were all non-medical uses of EEG such as self-improvement or controlling video games. However, this has changed in recent years with the advent of small, inexpensive, and easy-to-use EEG headsets designed to be used by members of the general public rather than medical professionals and researchers. Typically, these consumer orientated EEG headsets exploit a small number of electrodes (e.g. 2-12), in contrast to the hundreds employed in medical and research systems. Such headsets are worn by the user throughout a neurofeedback activity, which typically last between a few minutes and an hour.

Early consumer EEG headsets were still relatively stationary, and coupled to fixed electronic devices (FEDs)—primarily desktop and laptop computers. However, due to the recent explosive market penetration of portable electronic devices (PEDs) such as personal digital assistants, smartphones, and tablet computers, this has begun to change. Certain consumer EEG devices have now been released that can interface with PEDs. Consumer EEG devices linked to PEDs have numerous advantages over consumer EEG devices that interface with FEDs. Such benefits include localized wireless interfacing, e.g. Bluetooth; portability. as EEG headsets interfaced to PEDs can be used essentially anywhere, and—since PEDs now outnumber FEDs—access to a larger market Despite the great potential consumer EEG—especially PED-linked consumer EEG—has for medical, self-monitoring, and self-improvement applications, it is usually still treated as a novelty or toy, and used almost solely for entertainment purposes. Much of this has to do with limitations in development tools and supporting programs, which are geared primarily towards stationary use and games, which makes it difficult to create other types of software for consumer EEG. Also, these tools are geared toward developing applications intended for short-term use, and as such do not support numerous uses of consumer EEG applicable only when the devices are used for longer periods and/or continuously throughout the day, such as uses applicable to embedding EEG-based BCI into everyday activities or for the tracking of user medical information recorded throughout the day by EEG. Furthermore, existing development tools for consumer EEG are not conducive to web integration, which makes it nearly impossible to create consumer EEG applications that do such things as link EEG data to existing global databases, integrate EEG data with social media, send user EEG data to a dedicated server for deeper analysis than is practical on a smartphone, etc.

Another limitation in the prior art relating to neurofeedback and consumer EEG devices is the number of detectable and alterable mental states, which have mostly been confined to level of attention, relaxation, stress, and quality of sleep. Outside of academic research, the detection and alteration of states of mental clarity—which could otherwise be called level of mental fogginess, cognitive tempo, acute intelligence, mental "sharpness," cognitive performance, or level of mental confusion—have been ignored. This state is associated with numerous forms of mental/cognitive processing and abstract thought, such as ability to reason and current level of creativity. Mental clarity is a detectable metric, as is strongly suggested by research on a phenomenon called "feature binding," which is a person's ability to link information from different sources together to solve problems or be creative. On a simpler level, this can simply be the combination of 2 different types of sensory information coming in from different modalities to solve a small puzzle—for example figuring out what a particular object is when presented with a colour and a shape separately (e.g. the colour red is shown at one point, and a semi-circular shape later on, and the person is able to connect the separate pieces of information to determine that the object is an apple); see Keizer et al, 2010 in "Enhancing Cognitive Control Through Neurofeedback: A Role of Gamma-band Activity in Managing Episodic Retrieval" (Neuroimage, 49(4): p3404-3413)

Furthermore, the detection and alteration (through neurofeedback) of meditative states has primarily been treated as synonymous with relaxation, despite the numerous differences in the brain activity observed between relaxation and meditation. Meditative states also relate strongly to other detectable mental states—most notably level of attention. This fact has been largely ignored in algorithms used in previous embodiments of the invention.

According to embodiments of the invention the inventors have established new technologies and solutions that address these limitations within the prior art and provide benefits including, but not limited to, global acquisition and storage of acquired EEG data and processed EEG data, development interfaces for expansion and re-analysis of acquired EEG data, long-term/continuous user wearability, detection of states of mental clarity, and improved detection of states of meditation.

Other aspects and features of the present invention will become apparent to those ordinarily skilled in the art upon review of the following description of specific embodiments of the invention in conjunction with the accompanying figures.

SUMMARY OF THE INVENTION

It is an objective of the present invention to mitigate drawbacks within the prior art relating to EEG-based brain activity monitoring devices, and more particularly to portable systems for brain activity recording, storage, analysis, and neurofeedback that operate in conjunction with an application and web-based framework for more extensive storage and analysis.

In accordance with an embodiment of the invention there is provided a method comprising: receiving electroencephalography (EEG) data relating to a user; generating processed EEG data by applying a first processing algorithm to the obtained EEG data; transferring the processed EEG data to a remote storage device together with at least a unique identity of the user.

In accordance with an embodiment of the invention there is provided a system comprising:

a first interface operating according to a predetermined standard for receiving electroencephalography (EEG) data relating to a user from a portable electronic device associated with the user;

a storage device for storing the received EEG data;

a microprocessor for executing a software application applying at least a first processing algorithm to a predetermined portion of the stored EEG data to generate processed EEG data and establishing an outcome in dependence upon at least the processed EEG data;

a second interface for communicating the outcome to the portable electronic device for presentation to the user.

In accordance with an embodiment invention there is provided a device comprising:

a headband to fit around the back of a user's head;

a pair of arms connected to the headband projecting forward to fit along the sides of the user's head and for supporting the front of the device by the user's ears;

a pair of support guides, each coupled to an arm;

a pair of first electroencephalography (EEG) sensors, each first EEG sensor disposed upon a support guide;

a pair of second EEG sensors disposed within the headband.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures, wherein:

FIGS. 1A through 1C depict EEG sensor electrode configurations for obtaining EEG signals from a user with non-amplified "passive electrodes";

FIG. 1D depicts a drive circuit for amplifying an EEG signal obtained with an EEG sensor to convert "passive electrodes" to "active electrodes" with increased resistance to movement;

FIG. 1E depicts an exploded view of a novel sensor electrode configuration according to an embodiment of the invention;

FIG. 2A depicts an exemplary EEG system configuration according to an embodiment of the invention;

FIGS. 2B and 2C depict exemplary configurations of EEG detection and EEG Control Systems as depicted within FIG. 2A;

FIG. 3C depicts an EEG headset configuration according to an embodiment of the invention providing extended user wearability according to embodiments of the invention;

FIG. 9 depicts typical EEG bands for an adult in each stage of sleep;

FIGS. 10A and 10B depict a typical EEG spectrum for an adult together with the typical EEG bands for an adult;

DETAILED DESCRIPTION

Figure 3A:
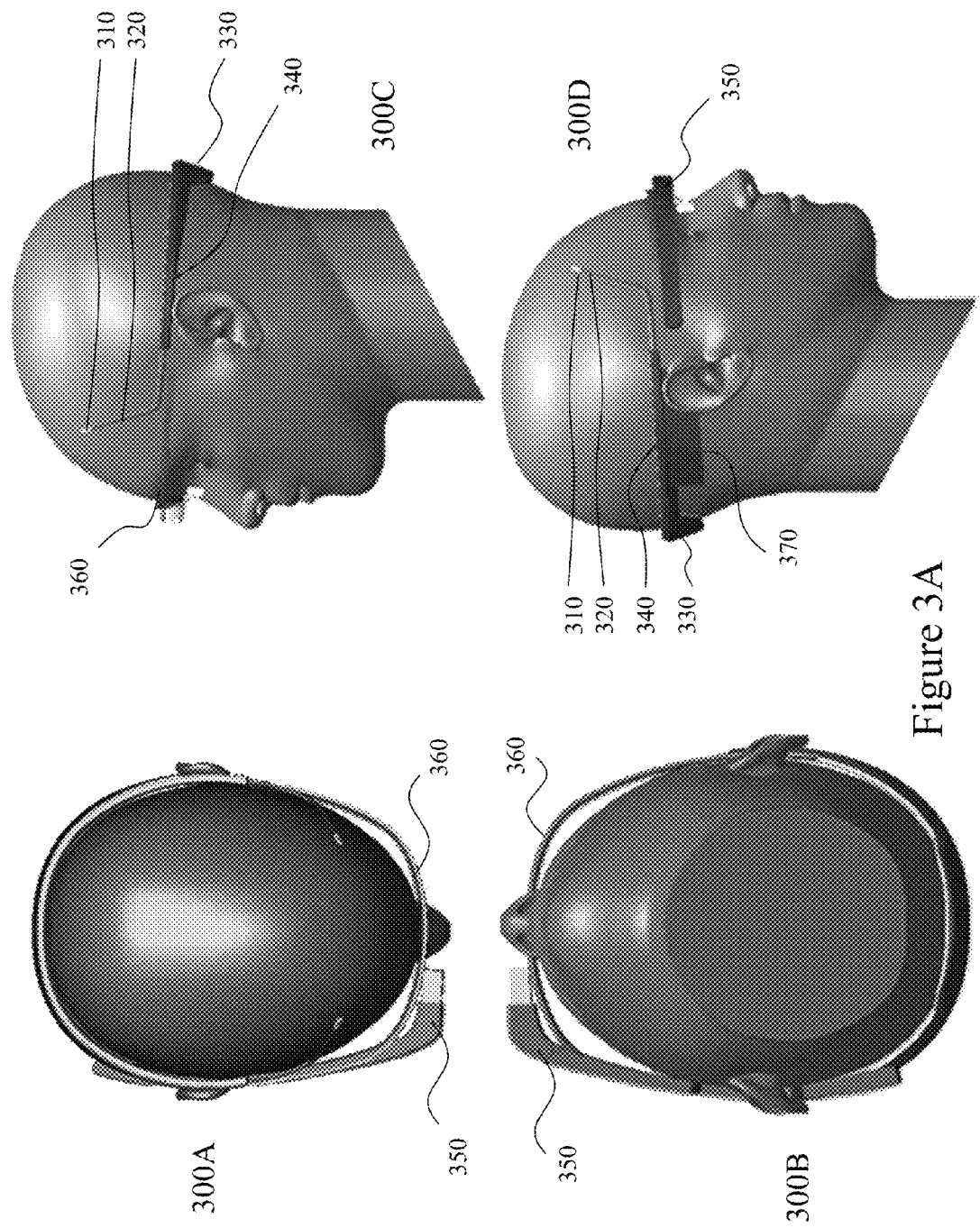
FIGS. 3A and 3B depict an EEG headset configuration according to an embodiment of the invention providing extended user wearability according to embodiments of the invention.

The present invention is directed to EEG-based brain activity monitoring devices, and more particularly to portable systems for brain activity recording, storage, analysis, and neurofeedback that operate in conjunction with an application and web-based framework for more extensive storage and analysis.

The following description provides exemplary embodiment(s) only, and is not intended to limit the scope, applicability or configuration of the disclosure. Rather, the following description of the exemplary embodiment(s) will enable those skilled in the art to implement an exemplary embodiment. It being understood that various changes may be made in the function and arrangement of elements without departing from the spirit and scope as set forth in the appended claims.

A "portable electronic device" (PED) as used herein and throughout this disclosure, refers to devices used for wireless communications and other applications that requires an energy storage unit such as a battery for power. These include (but are not limited to) cellular telephones, smartphones, personal digital assistants (PDAs), portable computers, pagers, portable multimedia players, portable gaming consoles, laptop computers, tablet computers, and electronic readers.

A "fixed electronic devices" (FED) as used herein and throughout this disclosure refer to wireless and/or wired devices used for communications (and other applications) that require a connection to a fixed interface to obtain power. These include (but are not limited to) laptop computers, personal computers, computer servers, electronic kiosks, stationary gaming consoles, digital set-top boxes, Internet-enabled appliances, Internet-enabled televisions, and stationary multimedia players.

An "EEG Assembly" as used herein and throughout this disclosure, refers to an assembly worn by a user that includes one or more EEG sensors for recording changes in scalp voltage resulting from brain activity (EEG data). Certain embodiments of the invention include one or more reference sensors—generally placed on one or both of the ears, the nose, or potentially the mid-neck to upper-neck—for recording reference signals. These signals are intended to be subtracted from the voltages recorded from the EEG sensor. Other embodiments may instead use an "average reference," where no specific reference electrode is used, with the average signals from all electrodes used as a reference instead. Various embodiments of the invention may include assemblies which are interfaced wirelessly and/or via a wired interface to an associated electronics device (either PED or FED) providing at least one of: pre-processing, processing, and/or analysis of the EEG data discretely or in conjunction with the reference signal(s). Said EEG Assembly may be wirelessly connected and/or wired to an ancillary electronic device, such as a PED or FED, to provide recording, pre-processing, processing, and analysis of the EEG data discretely and/or in conjunction with reference signal(s); as well as supporting other functions including, but not limited to, Internet access, data storage, sensor integration with other biometric data, user calibration data, and user personal data. Such an EEG Assembly may be employed with or without additional elements such as a headset and/or support.

Referring to FIG. 1A there are presented perspective 100A and sectional views 100B of an EEG electrode which is an example of an EEG electrode, and does not account for all variations allowing exploitation of a metal contact to record skin/scalp voltage. The EEG electrode may be one or more different shapes including, but not limited to, circular, elliptical, square, rectangular, triangular, regular N-sided polygon, and irregular N-sided polygon. Alternatively, it may take the take the form of clips/snaps that fasten to the skin, or a small needle inserted through a small electrode base or EEG cap. As depicted, the EEG electrode comprises a base 103 formed, for example, of foam, a fabric, a nonwoven fabric, or a tape including synthetic polymer and natural polymer, and is optionally provided with an acryl-grouped biocompatible adhesion paste deposited on one surface thereof; a stiffener 102 made of polymer and attached to the other surface of the base 103 for preventing evaporation of moisture; a snap 101 made of metal, for example brass and installed at the central portion of the stiffener 102, and an electrode element 104, for example made of plastic reinforced with glass fiber and deposited with silver/silver chloride, the snap 101 and the electrode element 104 being fixed to each other; a conductive hydro gel adhesive agent 105 coating the exposed surface of the electrode element 104; and a release film 106 attached to the hydro gel adhesive agent 105 and the remaining adhesion paste on the base 103 for protecting the hydro gel adhesive agent 105 and the remaining adhesion paste on the base 103. The EEG electrode may optionally use a conductive adhesion gel, glue, or adhesive tape for attaching the assembly to the skin, for example on the forehead, temple, and/or one earlobe or both earlobes.

Although FIG. 1A does not depict this, an EEG electrode may also optionally use a pad for soaking in a conductive liquid solution for improving conductivity between the scalp and electrode, or optionally require soaking in a liquid solution for improving conductivity without the presence of a pad. Other EEG electrodes may also optionally use a thin needle to produce connectivity between the electrode and the skull surface—rather than the scalp. The skin below the location where an EEG electrode is placed may optionally be lightly scraped to remove detritus such as dead skin cells that may lower conductivity between the scalp and the EEG. In cases where an EEG electrode uses a conductive adhesion gel or glue, and/or a conductive liquid solution or needle, and/or requires scraping of the skin below the electrode, a period of time for preparation may be required. These techniques for increasing conductivity and all aforementioned methods of preparation can also be used with active electrodes, such as that depicted in FIG. 1B 100C.

Referring to FIG. 1B there is depicted a cross-sectional view 100C of an example of an active dry sensor electrode for the measurement of scalp voltage in accordance with an embodiment of the invention comprising an active electrode 154, a resilient member 155, such as a spring, an amplification circuit 157, a main body 153, and a holder 152 and a cap 151 necessary for fixing the sensor module 100C when the sensor module 100C is installed in a headset 160. The active electrode 154 is interlocked with the cap 151, and vertically slides relative to the cap 151. The upper part of the active electrode 154 is exposed to the outside to contact skin of a user, such as via optional disposable pad 150. The main body protrusion which restricts the movement of holder 152 which latches to the cap 151 when inserted so that the lower portion of the active electrode 154 projects from the surface of the cap 151 when attached to retain the active dry sensor electrode within the headset 160. The active electrode 154 is the element either directly contacting the scalp wherein the active electrode 154 measures a biomedical signal, for example, EEG, or via optional disposable pad 150. The resilient member 155 is retained laterally within the active dry sensor electrode by retainer 158 whilst the amplification circuit 157 is mounted upon spacer 156 within the main body 153. Main body 153 may be sectioned such that it assembles laterally around the active electrode 154, amplification circuit 157, resilient member 155 etc. or section for assembly vertically, e.g. by attaching a second part of the body to the first when the resilient member 155 is inserted through the amplification circuit 157 and retainer 158 assembled.

Accordingly, since the reliability of the measured value of the EEG signal depends on the active electrode 154 having good contact with the scalp, then the active electrode 154 may be plated with another material such as gold, silver, or indium tin oxide (ITO) to improve the conductivity of the active electrode 154 and allow electrical current to easily flow through the active electrode 154. Similarly, optional disposable pad 150 would be electrically conductive, such as for example through the use the use of an electrically conductive polymer and / or the use of a coating with an electrical conductor such as a metallic thin film, ITO thin film, or electrically conductive polymer. As depicted, amplification circuit 157 receives the electrical voltage from the user's scalp and electrically amplifies the signal using an amplification circuit such as that depicted in respect of FIG. 1D or in FIG. 4. Active electrode 154 may similarly be formed from a conductive plastic or be a plastic with a conductive coating. Optionally, the surface of the active electrode 154 and / or optional disposable pad 150 may be concave or toothed so that the contact surface has stable, long-lasting contact with the scalp of the user. A concave active electrode 154 may for example be used to directly contact a bare portion of the scalp whilst a toothed active electrode 154 may provide contact to a portion of the user having hair on the scalp.

Referring to FIG. 1C there is depicted an active electrode 100D according to an embodiment of the invention. As depicted, active electrode 100D comprises a carrier 175 onto which a flexible circuit 174 is mounted. On the first and second contact pads 176 and 178 are embedded the first and second contacts 177 and 179, respectively, which are coupled via carrier 175 and flexible circuit 174 to integrated circuit (IC) 172. Also mounted to flexible circuit 174 are discrete components 171 representing inductors, resistors, and capacitors required for the IC 172. Within active electrode 100D IC 172 is coupled to a remote device via cabling 173 which may for example include power, signaling to IC 172, and signaling from 172. Optionally, IC 172 may be locally powered through a thin film battery source rechargeable wirelessly and/or include a wireless interface such that signaling is provided wirelessly. Optionally, cabling 173 may provide low voltage DC power only. First contact 177 in conjunction with first contact pad 176 may provide an EEG sensor, with second contact 179 and second contact pad 178 providing a second EEG sensor for detecting scalp voltage/receiving EEG data at a location extremely near to the location where first contact 177 and first contact pad 176 are detecting scalp voltage/receiving EEG data. Optionally, second contact 179 and/or second contact pad 178 can be omitted, or alternatively, first contact 177 and/or first contact pad 176 can be omitted. Also, first contact 177, first contact pad 176, second contact 179, and second contact pad 178 can be used in tandem to act as one single electrode. An average voltage can be taken between first contact 177 and first contact pad 176, and second contact 179 and second contact pad 178 to produce a single voltage reading of greater accuracy than that which could be taken from a single contact electrode.

Referring to FIG. 1D there is depicted an exemplary amplifier circuit for an EEG sensor such as depicted in respect of FIGS. 1A through 1C wherein an EEG electrode 185 has its output coupled to a second differential amplifier 180B wherein the second input of the second differential amplifier 180B is the output of a first differential amplifier 180A which is coupled to a reference signal, denoted as $V_{REF}$, such that the output of the second differential amplifier 180B is a reference corrected signal, $V_{OUT}$. As depicted both the first and second differential amplifiers 180A and 180B respectively are coupled to positive and negative power rails $V_{DD}$ and $V_{SS}$ respectively. The reference signal, $V_{REF}$, may be derived for example from a precision voltage reference, a voltage derived from an IC such as IC 172, and/or from a reference sensor/electrode.

The electrical signal emitted from the scalp that EEG data is comprised of is very weak: in the order of microvolts. Accordingly, it is not easy to detect such signals with the typical amount of noise which may arise from multiple sources, including but not limited to the circuit itself, external sources such as wireless transmitters, background skin voltage, and non-relevant sources of change in voltage in the detected signal, for example those arising from the sensors such as dry contact sensor(s), wet contact sensor(s), or non-contact EEG sensor(s). Accordingly, some embodiments of the invention reduce the noise using a reference electrode otherwise known as a "common reference" meaning an electrode placed at a location unaffected by the electrical activity of the brain, but still affected by all of these sources of noise. The voltage detected by the reference electrode is subtracted from the voltage detected by the EEG electrode, which results in a waveform that only contains sources of variance in voltage that are unique to the EEG electrode, which means only brain activity-related changes in voltage should be present. Other embodiments of the invention reduce the noise using an "average reference" method instead, in which the average voltage detected by all electrodes is subtracted from each individual electrode's voltage. Since brain activity varies more across different locations on the skull than other sources of variance in the voltage, subtracting the average voltage across all electrodes should only result in subtracting waveforms that don't occur as a result of brain activity (since the brain-activity related waveforms should be relatively unique at different places on the head).

Now referring to FIG. 1E there is depicted a unique electrode design created by the inventors that makes it easier to read scalp voltages / receive EEG signals through the user's hair. As depicted, multiple small conductive metal cylinders / wide-topped flat pins 187 are soldered onto a small conductive metal plate 188. Although 13 wide-topped flat pins 187 are depicted in FIGS. 1E, the number of pins 187 soldered onto the conductive mental plate 188 can vary, as long as there are at least 3 pins to prevent piercing the skin of the scalp. The bottom of small conductive metal plate 188 (the side opposite to the conductive pins 187) is attached to an electrically insulating plate 189. A metal "lid" 186 with holes 190 punched in it that directly fit the configuration of pins 187 is attached to the other side of conductive metal plate 188, with pins 187 slid through the holes 190. The inner rim of metal "lid" 186 is soldered to the inner rim of electrical insulator plate 189. A wire 191 may pass through a hole 191 (depicted in Figure lE) in electrical insulator plate 189 to connect to electrical conductor plate 188.

The pins 187 and conductive metal plate 188 in FIG. 1E can be made out of any solid conductive material or combination of materials, including (but not limited to) metals such as copper, silver, silver chloride, aluminum, tin, gold, iron; metal chlorides such as silver chloride; conductive polymers such as polyaniline, poly(3,4-ethylenedioxythiophene)/PEDOT, or polyphenylene vinylene; plated metals such as tin-plated copper, gold-plated copper, or silver-plated copper; conductive metal alloys such as copper-magnesium alloy, lead-tin alloy, tin-lead-silver alloy, copper-silver-alloy, or copper-silver-zinc alloy; or carbon-based conductive materials such as graphite, graphene, colossal carbon tubes, conducting carbon nanotubes, conducting metallic nanotubes, or IsoNanotubes™. Electrical insulator plate 189 can be made out of any non-conductive/insulating material or combination of materials, including (but not limited to) glass; electrical insulation paper; ceramics such as porcelain, aluminium oxide, or sintered beryllium oxide; non-conductive polymers/plastic such as polyvinyl chloride (PVC), Kapton, ethylene tetrafluoroethylene (ETFE), or Teflon; or nonconductive composite materials. Metal lid 186 can be made of any material that can be strongly bonded to electrical insulator plate 189.

FIG. 2A depicts a block diagram illustrating an EEG system in accordance with some embodiments of the invention which comprises an EEG Detection System 230 for picking up EEG signals from a user, an EEG Control System 210 for doing initial processing on the data and preparing it for digital transmission, and a System under Control (SUC) 250, which is any hardware or software that can be communicated with by (and can alter its behavior in response to) EEG data outputted from EEG Control System 210. Some embodiments of the invention can have each of these components built into a separate device, rather than having all 3 components built into the same system. In one exemplary embodiment, EEG Detection System 230 is contained in an EEG headset that is attached in a wired or wireless configuration to a separate device containing EEG control system 210, which sends EEG data via another wired or wireless interface to a PED for example. Other embodiments may integrate the EEG Control System 210, EEG Detection System 230 and SUC 250 into one device. Other embodiments have the EEG Control System 210 and EEG Detection System 230 integrated into a single device generally a one-piece headset, for example, that detects EEG signals from the skull and transmits them to SUC 250 either through a wired or wireless interface. Still other embodiments have the EEG Detection System 230 in its own standalone device which transmits completely unprocessed EEG data to a PED or FED containing an implementation of EEG Control System 210 and SUC 250 which may be implemented in hardware and/or software.

In some embodiments of the invention, the EEG Control System 210 sends corresponding control signal(s) to the SUC 250, whilst in other embodiments the EEG Detection System 230 sends raw EEG signal data, or in some embodiments processed EEG signal data (e.g. to filter out noise) to the EEG Control System 210. FIG. 2B depicts a functional diagram illustrating EEG Control System 210 in accordance with some embodiments of the invention wherein the EEG Control System 210 includes an EEG Detection Communications 211 module for communicating with the EEG Detection System 230, a Processor 212 for applying analysis algorithms to EEG signals detected by EEG Detection System 230 in order to, for example, generate spectral power values for wavebands (delta, theta, etc.) based on specific frequency ranges, an Output Control 213 for communicating with the SUC 250, a Local Communications 214 for communicating with one or more local devices and/or interfaces, and a Data Storage 216 which may for example provide functionality for storing received EEG signal samples and associated timing data such as for the audible, visual and tactile cue patterns/frequencies etc. These are linked via an internal Communication Link 2151n certain embodiments of the invention, EEG Control System 210 contains a component for sending detected EEG signal samples to a computer, which in some embodiments includes a processor configured to run algorithms—such as spectral decompositions—on the EEG signals it receives from EEG Detection System 230. Following the analysis, the microprocessor can then provide the resulting metrics, such as for example spectral power values for specific wavebands, to other components of the system, which can include the EEG Control System 210 and/or the SUC 250 based on the results of the analysis of the EEG signal samples. In some embodiments, all or just a portion of the analyses of the EEG signal samples are performed by the programmed computer, while in other embodiments, all or just a portion of the analyses of the EEG signal samples are performed in EEG Detection System 230, EEG Control System 210, or both; e.g., using an Application Specific Integrated Circuit (ASIC) or Field Programmable Gate Array (FPGA) integrated with or in communication with EEG sensors. Following the analyses, the EEG data can be put to functional use, such as to e.g. directly control the device or to communicate the user's mental state.

FIG. 2C depicts a functional diagram illustrating an EEG Detection System 230 in accordance with some embodiments of the invention wherein the EEG Detection System 230 includes a Processor 232, e.g., an FPGA, ASIC, or microprocessor, an EEG Sensor 231, an EEG Reference Sensor 234, an Output Control 233 for communicating with EEG Control System 210, and an internal Communication Link 235. Measured EEG signals are provided to the EEG Control System 210 by Output Control 233 following local processing by Processor 232 and appropriate voltage correction based upon the associated EEG Reference Sensor 234. Calibration data, user data, information about processes currently in execution by Processor 232, and other data associated with the EEG Detection System 230 are stored within local Storage 236. In some embodiments, a continuous stream of EEG signal samples are detected and provided to the EEG Control System 210, whilst in other embodiments these are periodically transmitted, averaged and filtered prior to transmission, and only transmitted when/if certain predetermined criteria are met.

Prior to analysis and all other forms of data cleaning and pre-processing, the voltage of the reference electrode is subtracted from that of the EEG electrode(s). As discussed earlier, this immediately removes a great deal of noise from the data. The data is then run through a variant of the Discrete Fourier Transform, e.g. a Fast Fourier Transform (FFT) within some embodiments of the invention, to decompose the EEG data into constituent EEG waveforms/neural oscillations. The result of the FFT is then spectrally analyzed using high- and low-pass filters that are applied to restrict the EEG data to a frequency range where brainwave activity is relatively easy to identify. For example, typically 1-50 Hz is wide enough to include all of the classic EEG wavebands (e.g. theta, delta), but not so wide as to include frequencies that are excessively prone to contamination by artifacts. Artifacts are voltage spikes and/or troughs caused by phenomena other than brain electrical activity—such as small muscle movements or heartbeat. Although the data will still be affected by artifacts regardless of what frequency range is chosen, restricting the range as such reduces the degree of contamination. Optionally, the EEG data may be filtered prior to the FFT process.

Accordingly, it would be evident that the inventors primarily exploit an EEG analysis system based on neural oscillations/"non-phase-locked induced rhythms" to determine the user's background mental state, rather than using a system based on examining evoked potentials/evoked activity, such as those that focus on the analysis of event-related potentials (ERPs), steady-state evoked potentials (SSEPs), visual evoked potentials (VEPs), or steady-state visual-evoked potentials. Although other embodiments can include functionality relating to some of these other frameworks for EEG data analysis, they are not necessary, and do not play a primary role in any core aspect or feature of this invention.

Consider "Introspect" a multi-purpose software bundle by the inventors that as part of its features provides users with a series of EEG-derived numerical metrics,—e.g. a numeric rating of how positive or negative their current mood is, so that they can track aspects of their brain health. Scores on the main functions/metrics of interest discussed in greater detail below, are established entirely through EEG waveform analysis. "Introspect" uses these scores to recommend specific built-in neurofeedback-based exercises intended to improve areas of weakness for the user. These EEG waveform-dependent results will be reported to users in the form of visual elements such as graphs that show progress in specific areas over time, which will be displayed on a dashboard-type User Interface (UI). Areas of interest can be selected by users for inclusion on the dashboard, to avoid displaying unnecessary information (e.g. only epileptics would be interested in seizure data). The portability of the headset and software will allow users to take readings throughout the day, including if users activate the option reminders to perform scans. This will help prevent all readings from being taken in the same states of mind (e.g. states in which users are self-motivated enough to use the software), and/or at the same general times of day (e.g. before and after work). Avoiding these issues will allow "Introspect" to collect data that is much more representative of the user's day-to-day mental life, i.e. the data is more meaningful and thus useful. "Introspect" may trigger self-report measures, for example based upon questionnaires presented randomly throughout the day, at requested intervals, and/or when users choose to fill them out. For example, a clinical neurophysiologist monitoring a user exploiting more extensive software analysis algorithms than those on the user's PED may trigger such questionnaires on their own or in combination with the "Introspect" software. It would be evident that this information may be used in tandem with the EEG readings to generate more comprehensive data and more accurate results. This more comprehensive data would result in neurofeedback exercise suggestions that are better-targeted to the user's mental weaknesses, resulting in greater improvements.

Mental states which the EEG waveform analysis roughly quantifies and displays to users in the form of a metric may include, but are not limited to, stress, relaxation, concentration, meditation, emotion and/or mood, valence (positiveness/negativeness of mood), arousal (intensity of mood), dominance (feeling of "control"), anxiety, drowsiness, state mental clarity/acute cognitive functioning (i.e. "mental fogginess" vs. "mental clarity", creativity, reasoning, memory), sleep, sleep quality (for example based on time spent in each stage of sleep as easily detected with EEG), amount of time asleep, presence of a seizure, presence of a seizure "prodromal stage" (indicative of an upcoming seizure), presence of stroke or impending stroke, presence of migraine or impending migraine, severity of migraine, heart rate, panic attack or impending panic attack.

Biomarkers for numerous mental and neurological disorders, to aid in screening and diagnosis, may also be established through biosignal detection and analysis, e.g. using EEG signals. In addition, multiple disorders are expected to have detectable EEG footprints with increased EEG sample acquisition for a single user and increased user statistics/data. Such disorders may include, but are not limited to, depression, bipolar disorder, generalized anxiety disorder, Alzheimer's disease, schizophrenia, various forms of epilepsy, sleep disorders, panic disorder, ADHD, and autism.

Accordingly, after EEG data obtained from a user is pre-processed as discussed previously, the spectral power of each selected frequency EEG band is extracted on a block-by-block-basis, with blocks defined as stretches of raw EEG voltage value samples. Blocks 1 second long with approximately 512 voltage samples are employed according to an exemplary embodiment of the invention although different block lengths and voltage samples/block can be used. The specific frequency ranges of each EEG band in an exemplary embodiment of the invention are delta at 1-3Hz, theta at 4-7Hz, low alpha at 8-9Hz, high alpha at 10-12Hz, low beta at 13-17Hz, high beta at 18-30Hz, low gamma at 31-40Hz, and high gamma at 41-50Hz. Other embodiments of the invention can use other frequency bands, such as those depicted in FIGS. 9 and 10B. Optionally, this determination may be weighted, for example through a cluster analysis process, with additional information derived from other biosensors, location information, and other information derived by the overall EEG system associated with the user such as described below for example in respect of FIG. 12 wherein the user's PED may for example associate heart rate and pulse biosensor information together with location in determining a user's mental state. Optionally, the EEG data may be pre-processed, or left raw, before being processed in preparation for feature classification, i.e. mental state classification using an FFT process described for the exemplary embodiment of the invention although other feature classification processed may be employed. See FIG. 10A for an example of weightings of spectral content determined based upon FFT bin data for use in e.g. finding spectral power values for each selected EEG frequency band (as described above).

The amount of variance in the EEG wave that can be accounted for by each brainwave type may be calculated, producing numeric values for each selected EEG frequency band, generally based upon relative weightings of the spectral power in each band as listed in Table 3 and discussed supra. Based upon analysis of the resulting data generated for each frequency band and their weightings against one another, one or more features may then be extracted. An example of a feature extraction rule, which is simpler than those which will be implemented with the commercial products of the inventors, is given by Equations (1A) and (1B) for roughly quantifying a user's level of concentration.

$$((N_{THETA}-1) < (2 \cdot N_{BETA})) \text{ then Conc} = (2 \cdot N_{BETA} - N_{THETA}) \quad (1A)$$

$$((N_{THETA}-1) \geq (2 \cdot N_{BETA})) \text{ then Conc} = (1/N_{BETA}) \quad (1B)$$

where Conc is the weighting given to concentration and $N_{BETA}$ and $N_{THETA}$ are the numeric values for beta and theta brainwaves respectively.

It would be evident that other algorithms may be exploited. Examples of two novel two novel feature extraction rules established by the inventors are described below for mental clarity and meditation values.

Mental Clarity Extraction Algorithm: This exploits the low beta (13-17 Hz), low gamma (31-40 Hz), and mid gamma (41-50 Hz) ranges of EEG activity. Power in each waveband is fitted to a curve that removes artifacts related to the hardware of the EEG device and converts the raw EEG voltage data into a normalized 1 to 100 scale. These modified EEG values are then scaled against one another to form a conglomerate score for mental clarity. Equations (2)-(5) provide an exemplary embodiment of this metric developed by the inventors using 1s epochs of data to generate waveband values.

$$Adj\beta_L = \left((-(1.06^{\beta_L+75})=80) - \left|\frac{(\beta_L-30)(\beta_L-70)}{210}\right| + 10\right) + 15e^{-4.1e^{-0.25(\beta_L-70)}} \quad (2)$$

$$Adj\gamma_L = \left((-(1.06^{\gamma_L+75})=80) - \left|\frac{(\gamma_L-30)(\gamma_L-70)}{210}\right| + 10\right) + 15e^{-4.1e^{-0.25(\gamma_L-70)}} \quad (3)$$

$$Adj\gamma_M = \left((-(1.06^{\gamma_M+75})=80) - \left|\frac{(\gamma_M-30)(\gamma_M-70)}{210}\right| + 10\right) + 15e^{-4.1e^{-0.25(\gamma_M-70)}} \quad (4)$$

$$Score_{CLARITY} = \frac{3Adj\gamma_M + 2Adj\gamma_L + Adj\beta_L}{6} \quad (5)$$

where $Adj\gamma_L$ is the current adjusted power in the low-beta EEG band; $Adj\beta_L$ is the current adjusted power in the low-gamma EEG band; $Adj\gamma_M$ is the current adjusted power in the high-gamma EEG band; $\beta_L$ is the current (unadjusted) power in the low-beta EEG band; $\gamma_L$ is the current unadjusted power in the low-gamma band, $\gamma_M$ is the current unadjusted power in the high-gamma band; and $Score_{CLARITY}$ is the clarity score for the current 1 second epoch.

Meditation Value Algorithm: This involves the use of a metric for relaxation, generally on a scale of 1 to 100, and a metric for attention. The meditation value is generated by taking whichever of these two values is the lowest, and then in some cases adding a portion of the distance between the lower value and higher value. Meditation is a state of relaxed attention, and it is thus especially important that both be present for a state to be considered meditative. We considered meditation quality primarily in terms of which value is the weakest to account for the essential requirement that both be present. The metrics for relaxation and attention may be generated using algorithms known within the prior art.

In addition to the algorithms discussed supra Personal Neuro Devices algorithms are primarily centered on spectral density analysis of raw EEG data (scalp voltage). Such analyses involve estimating the strength/spectral power of specific selected wavebands/EEG frequency ranges (with ranges measured in Hz e.g. 3-8 Hz), then sometimes comparing them against each other, e.g. calculating the ratio of the 0-4 Hz waveband's spectral power to that of the 10-12 Hz band. Because so many different waveband ranges can be selected, and so many comparisons made between selected wavebands' power values, spectral analysis on its own is able to extract a huge number of discrete features from the raw EEG data.

PND's algorithms may, for example, exploit a predetermined set of standard wavebands ranges such as those commonly used in EEG research or alternatively specific waveband ranges may be established for specific algorithms to enhance their accuracy based upon extended analysis. Standard wavebands may include, for example, the mu rhythm (~8-14 Hz), the sensorimotor rhythm (~12-15 Hz), and wavebands classified as the delta (~0-4 Hz), theta (~4-8 Hz), alpha (~8-12 Hz), low alpha (~8-10 Hz), high alpha (~10-12 Hz), beta (~12-30 Hz), low beta (~12-20 Hz), high beta (~20-30 Hz), and gamma (~30-50 Hz) bands. These common bands can be particularly useful as in many instances the ranges are defined in the research literature based on mental phenomena they are closely coupled to. For example, high spectral power levels in the "high beta" waveband is associated with anxiety because higher spectral power is seen in this range in anxious subjects and because neurofeedback techniques that reduce spectral power in this frequency range can reduce anxiety.

In addition to spectral power based determinations asymmetry-based methods may be employed in isolation or in conjunction with spectral power analysis to compare activity occurring in electrodes in one part of the brain with activity in electrodes in another. This comparison may, for example, be left and right hemispheres of the brain, due to the importance of left-right asymmetry for detection of mood valence (positiveness versus negativeness of mood. Since this has major implications for the detection and possible treatment of mood disorders, i.e. one of the world's biggest medical causes of mortality and lost productivity this is an important expansion in the analysis technique.

Entropy & fractal dimension analysis may also be applied to provide analysis of the complexity and irregularity of an EEG signal. In other words, they measure how "chaotic" the signal is. More random-seeming signals have a higher number of fractal dimensions, and higher entropy scores in general. These methods can be particularly useful for us because of the ease with which they can be implemented using pseudocode methods of calculating a data set's fractal dimension value. Such analysis may also be particularly effective when there are a restricted number of electrodes and when used in combination with other analytical methods, this type of analysis is able to generate a fair number of neurometrics with a reasonable degree of accuracy. These can include 2 dimensions of emotional state, namely arousal and valence together with attention levels.

Alternatively, linear time domain-based features, typically simple features, can be extracted from EEG data which have predictive value for some Neurometrics as well as disorders, stages of sleep, etc. particularly when used with other more complex feature analysis. Accordingly, through a combination of local algorithmic features, i.e. on the user's PED, and remote algorithmic features, i.e. those processing statistically or algorithmically extracted EEG data with machine learning classifiers running on remote servers, e.g. a cloud sourced backend, then these simpler features will essentially augment the more complex ones, to produce an overall greater classification accuracy. Examples of linear time-domain-based features that may be implemented/provided include, but are not limited to, the following:

- Zero-crossing rate. This refers to how many times the voltage passes from a negative-to-positive or positive-to-negative value per second. Inclusion of this measure has been shown to increase the accuracy of ensemble classifier-type algorithms that detect stages of sleep.

Further this feature is reasonably effective on its own at detecting certain discrete features in sleep that relate to sleep quality, such as sleep spindles.

- Mean (average) voltage.
- Variance.
- Skewness.
- Kurtosis. Useful in e.g. artifact removal.
- Average Peak Amplitude. Relating to average distance between consecutive peaks, with peaks being either extreme minimum or maximum voltages where its temporally neighbouring voltages on both sides, i.e. voltages recorded within a few milliseconds before and after the "peak" point are all higher (for minimum) or all lower (for maximum). This feature is useful for increasing accuracy of sleep stage detection when used with other features in classifier algorithms or for helping classify what task someone is performing (albeit in artificially restricted settings).

Amongst the neurometric-detection algorithms in use by PND are

- Clarity: wherein the "clarity" neurometric is based directly on the power values in the upper alpha range of EEG brainwaves (10-12 Hz) wherein power values produce higher scores. Individuals with post-concussion syndrome show reduced power in this range which may be related to impaired top-down processing, or an impaired ability to direct attention internally.
- Attention: wherein analysis of alpha and beta waves extracted from the raw EEG voltages provides a method of calculating users' attention levels.
- Relaxation: where frontal alpha and theta bands provide data for the analysis of relaxation and mindfulness. Different weights may be given to each band in the calculation of the index as the appearance of activity in each of the bands also depends on the expertise of the meditator. For example, if the user is able to produce alpha consistently for a period of time (which often dominates the brain activity of a novice meditator), additional weighting may be added to the theta band (seen in intermediate meditators) to encourage further relaxation.
- Mindfulness: wherein "mindfulness" values are calculated through a combination of their relaxation and attention levels. For example, an algorithm according to the inventors begins by subtracting the value of the lower metric (between attention and relaxation) from that of the higher metric and dividing the result by 3. This result is then added to the value of the lowest metric. Accordingly, a lower weighting is given to the higher of the two metrics simply because both relaxation and attention must be present for the user to be in a state of mindfulness; the score rewards users that concurrently increase both more than if a simple average of attention and relaxation was employed.
- Emotions: Certain emotions can be detected using restricted-electrode EEG through the combining of information from multiple EEG features that are indicative of emotional state to produce a strong prediction through ensemble classification techniques, especially those involving "boosting", such as bagging and AdaBoost. Examples of weak but significant predictors include differences in the symmetry of brain activity in relation to mood, with negative moods somewhat tending to produce greater activity in the right hemisphere, and positive ones in the left, although it is reversed in some people. Calibration methods exploited by PND include experience sampling, where the software periodically asks the user to rate how they feel a few times during the day, then compares the surrounding EEG activity to the self-rated mood to determine which direction the asymmetry goes in the user. Other predictors include the coupling between EEG delta and beta oscillations is enhanced in anxious states and the alpha peak frequency reducing during sadness and fear, but increasing during happiness and anger.
- Visuospatial Ability: the algorithm is based upon the power in the upper alpha band.
- Memory: wherein the algorithm for measuring memory activity is based on increasing power in the theta and decreasing power in the alpha bands.
- Processing Speed: where the calculation of an index for mental processing speed is based on the beta wave given the relation between beta wave activity and reaction times.

Other neurometric detection algorithms in use by PND relate to sleep quality, sleep quantity detection, stress, depression:

- Sleep Quantity: wherein sleep has characteristic patterns of EEG activity wherein each pattern of the multiple patterns is associated with a different stage and hence can be calculated simply by adding up the cumulative quantity of time any one of these patterns is present.
- Sleep Latency: also referred to as quantity of time it takes to fall asleep. Ultra-low sleep latency (0-5 minutes) is closely linked to fatigue and daytime feelings of sleepiness and is also a biomarker of narcolepsy. In contrast very high sleep latency indicates the presence of primary insomnia.
- Sleep Quality: Determined by the amount of time spent in each stage of sleep, and sleep continuity. Although, a very simple indicator can be based upon the time spent in stage 4 (slow wave) sleep and fewer nighttime awakenings
- Daytime Stress. Sleep EEG data cannot on its own detect daytime stress, but it can provide extra information that increases our ability to detect it when analyzed in tandem with daytime EEG data as stress within the preceding day is indicated by a reduction in REM, slow wave sleep, and overall sleep efficiency/sleep quality, as well as an increase in the number of middle-of-the-night awakenings.
- Depression: Where a user self-reports stressful events during the day but does not show the characteristic sleep pattern indicative of preceding-day stress, it's predictive of depression and may be a factor in screening for symptoms of depression wherein the degree of change in sleep pattern following a (self-reported) stressful day will be included in a multifactorial analysis as a single predictive factor. Further, biomarkers for depression have been identified in sleep EEG data separate this stress-related effect.

Introspect™ the multi-purpose software bundle by the inventors performs complex multifactorial analyses to provide users with a series of EEG-derived numerical metrics exploiting local and remote processing with backend algorithms and historical data. Accordingly, through the local and remote determinations of patterns in their data, such as potential underlying disorders (for screening, not diagnosis), Introspect™ will suggest a user see a doctor for a particular disorder if there are enough factors in place to suggest it may be present. In many instances the more accurate neurometrics for a user cannot be calculated on a PED and accordingly embodiments of the invention exploit neurofeedback based on quantitative EEG (qEEG) which is utilized in conjunction with cloud based backend processing via learning algorithms.

Quantitative EEG is an approach to EEG analysis, particularly neurofeedback, which requires the storage of large quantities of normative EEG data. qEEG involves taking and storing scans from a large pool of a certain type of research subject doing a particular task. Most commonly, the subject group is "healthy people" with no brain disorders, and the task simply a "resting state" wherein no task is explicitly defined except whether eyes should be open or closed. Features, such as power values in different wavebands, basic statistical components (e.g. mean voltage), and entropy scores etc. are then extracted from each subject's data. Average values of each feature over the whole scan are determined for each user. Whole-scan averages are then averaged between all users in the database, which generates normative values for each EEG feature in that population for that task. The more subjects and sessions there are stored in the database, the more accurate the normative scores will be. Accordingly, Introspect by virtue of pushing user data to cloud based and/or remote storage allows analyses to be performed upon a very large population base and further allows the population data to be divided by factors such as sex, race, and age.

Accordingly, databases established through Introspect™ can be used to automatically identify biomarkers of brain disorders, and as a result, aid diagnosis for users. Where a database of normative scores for a particular metric (on a particular task) exists for healthy subjects, a comparison can be made with average scores in a clinical population suffering from a specific disorder. Any differences found can then potentially act as biomarkers for the disorder, with their presence acting as diagnostic indicators, wherein the task plus scan can be used as a medical test to help diagnose said disorder.

Treatment-oriented neurofeedback in clinical populations can be guided by qEEG once biomarkers are identified. This involves taking the patient's EEG activity during the associated task (virtually always resting state for qEEG neurofeedback), then training them to produce EEG activity on the feature(s) similar to that generated by healthy controls. In other words, it "normalizes" disorder-associated brain activity. This has already proven effective for a number of brain disorders such as ADHD. As the Introspect™ backend database through all users contains an unprecedentedly large quantity of EEG data to be available over a diverse population of users both with and without various brain disorders.

Accordingly, Introspect can average scores on a wide variety of metrics for a wide variety of sub-populations, such as specific disorders and accordingly Introspect™ provides a very beneficial tool for the application of qEEG as in many instances the resting state data can be automatically extracted from the acquired EEG data. Classifier ensemble machine learning algorithms may constantly sort incoming data to use for each new metric to create more accurate normative values for healthy controls, such that qEEG data generated through Introspect will be of higher accuracy. Introspect™ may also run ongoing clustering analyses that will automatically sub-classify users based both on psychological and demographic variables, and their EEG metrics.

Additionally, Introspect™ may for certain types of groups, e.g. a population with a particular disorder, it will instead alert when it thinks it's found a sub-population. Introspect™ through its cloud based backend processing will allow conglomeration data of different types from multiple users in order to learn how to better calculate the neurometrics of interests, screen for disorders, provide lifestyle suggestions, and provide exercise suggestions. Numerous algorithms exist for this purpose, but of these support vector machines (SVMs) are potentially of most interest as these are learning methods intended for binary classification, that is, dividing data up to determine if it does or doesn't fit into a particular group or set of groups. The initial groups are defined based on "training data", that is, pre-classified existing data. The larger this training data set, the more accurate the SVM (as a rule of thumb). Further, SVMs can calculate the odds that their result is correct, and newer forms can perform regression classification, i.e. not just yes/no but that these return a decimal value similar to a Pearson's r value that is representative of the data point's correlation with a given group of interest. The basic idea of an SVM is to find a hyperplane (basically an n-dimensional plane—so a 3D, 4D, 5D or so on plane) that separates d-dimensional data into 2 classes. This isn't always possible in the number of dimensions of data there is, but we can get around this by increasing the number of dimensions until there is a hyperplane that can divide the data into 2 classes.

Prior art consumer EEG devices have been focused to either analysis of sleep quality, training specific patterns of activity, and/or on calculating levels of attention and relaxation/stress, which are typically exemplified by alpha, theta, beta, and delta brainwaves below approximately 30 Hz. However, real-time analysis of brainwaves with systems according to embodiments of the invention may also operate directly upon brainwaves characterized as gamma, at 31 Hz and above (although the exact frequency range of gamma may be defined as beginning at a slightly different frequency in certain cases). Neural network style learning, e.g. systems using multilayer perceptrons, may also be applied to the processed EEG brainwave data to determine particular patterns that occur with user actions/physical state such as determined through other biosensors or data acquired through the user's PED. For example, user brainwaves from playing a first person shooter game versus a motor racing game (or portions of a single game) may be associated with e.g. different FFT profiles or ratios of delta/theta/alpha/beta/alpha/gamma.

Referring to FIG. 3A there is depicted an example of a consumer orientated EEG detection system according to an embodiment of the invention established by the inventors. As depicted in first to fourth images 300A to 300D the user is wearing an EEG headset 330 in conjunction with a head mounted display (HMD) 350, e.g. Google Glass™. The HMD 360 is attached to a frame 360 similar to glasses such that it is supported on the user's ears and the bridge of their nose. It also comprises a controller 370 for communicating with an electronic device, e.g. a PED, via a wireless short-range and/or personal area network protocol. The EEG headset 330 in contrast mounts to the back of the user's head and comprises arms 340 that project forward to support guides 320 that end in EEG sensors 310. Through appropriate design of the arms 340, support guides 320, and EEG sensors 310 then the EEG headset 330 can measure at the temples of the user. Now referring to FIG. 3B the EEG headset 330 is depicted in isolation in first and third images 300E to 300G and in use in fourth image 300H. In second image 300F rear EEG contacts 380 are visible on either side of the rear of the EEG headset 330 such that these act in conjunction with the EEG sensors 310. Optionally, one of more additional pairs of electrodes may be disposed within EEG headset 330 including the arms 340, the support guides 320, and the body of the portion of the EEG headset 330 against the rear of the user's head. The support guides 320 and/or arms 340 may be shaped and formed from a material or materials allowing a flexibility in them such that when the EEG headset 330 is placed over the user's head slight pressure of the EEG sensors 310 against the user's head results.

As depicted as an isolated EEG headset 330 allows for reduced conspicuousness when worn by the user and it may in fact be offered with rear portion in a range of colours or with clip-on covers to support a wide range of colours allowing increased blending/reduced visibility of the EEG headset 330 against the user's hair and/or skin. However, it would be evident that the EEG headset 330 may also be incorporated into, for example, other types of headwear, such as a hat, motorcycle helmet, safety helmet, and flight helmet. Alternatively, EEG Detection System 230 or a variant of EEG Detection System 230 may be integrated into/incorporated with the EEG headset 330. Optionally, the EEG headset 330 may be incorporated with other wearable designs including, but not limited to, headphones, an application specific headset, ear-pieces, headbands, and headsets. As discussed earlier, In in many some instances the EEG sensors and all/part of the EEG Detection System 230, EEG Control System 210, and SUC 250 may be associated within the EEG headset 330 whilst in other embodiments of the invention the EEG Detection System 230 may be entirely/partially associated with the EEG headset 330 whilst the EEG Control System 210 and/or SUC 250 are interfaced by at least one of one or more wired interfaces, wireless interfaces and/or networks and housed within an electronic device, e.g. PED.

Accordingly, since EEG headset 330 or parts of EEG headset can be incorporated into / linked to / associated with wearable items of normal use and can thus be used during a day's regular activities, additional contextual association of the EEG determinations may be required such that the correct SUC 250 is communicated to, and that information specific to the function of the wearable item is included. For example, EEG data and metrics associated with mental states recorded whilst a user is wearing safety helmet in conjunction with EEG headset 330 or within which EEG headset 330 is integrated may include data relating specifically to user's activities whilst wearing the safety helmet such that a machine, e.g. PED, FED, or assembly line robot, when receiving the EEG data may act only when the data relating to safety helmet matches that within a database and / or a control system and / or memory location associated with the machine. Furthermore, certain item-specific information may be gathered by an item-specific peripheral attached to the user assembly. For example, a bicycle helmet may have a movement detecting device built into it to determine what speed a user is moving at, which could be set up such that the user assembly could receive information from it, which could also be transmitted to the machine, e.g. PED, FED, or electronic bicycle brakes. Alternatively, the user assembly may be set up such that certain forms of information are transmitted and / or certain algorithms are run on the EEG data only when the user assembly is incorporated into or associated with a specific device. For example, if incorporated into a safety helmet for use in a factory, the assembly may start running algorithms and / or transmitting data specific to detecting pain or head impacts, which if detected, could shut off the factory robot with which the user is working if pain and head impacts could be a result of injury generated by the machine as an added form of safety.

Accordingly, such a User Assembly could provide a user with mobile, continuous (or quasi-continuous), consumer-friendly, unobtrusive (EEG-based) mental state monitoring. It could also gather EEG data during events and tasks within which this was not previously practical—such as while riding a bus or working on a construction site. EEG measurements, EEG-based decisions, EEG-based BCIs, and EEG-based neural training and self-improvement techniques (primarily neurofeedback) could thus be integrated into the day-to-day life of a general consumer. The User Assembly's (or variants of the User Assembly's) comfort, ease-of-use, modularity, and—with certain iterations—ability to be easily incorporated into numerous forms of socially appropriate headwear will help promote consumer/market acceptance, i.e. widespread general-purpose use.

From the point of view of a programmer or clinician, all implementations/variants of the User Assembly should provide a good signal quality and two or more sensors (a minimum of one reference electrode, and one EEG electrode). Accordingly, amongst the factors affecting a User Assembly from the user's perspective are those listed in Table 1 below which have been grouped into broader categories for simplicity. As evident some criteria appear in in more than one category.

TABLE 1

| Design Factors for EEG User Assembly | | |
|---|---|---|
| Practicality | Sensors | Aesthetics |
| Cost | Number of sensors | Size |
| Size | Location of sensors | Location of sensors |
| Stability/wearability | Contact or non-contact sensors | Visibility of headset |
| Battery life | Active or passive electrodes | Conspicuousness of headset/sensors |
| Durability | Weight | |
| Weight | Cost | Modularity |
| Water resistance | Water resistance | Colour/Fashion |
| Modularity | Comfort | Customizability |

TABLE 1-continued

Design Factors for EEG User Assembly

| Practicality | Sensors | Aesthetics |
| --- | --- | --- |
| Comfort | Modularity | Material(s) used |
| Communications (wired or wireless) | Size | |
| | Material(s) used | |
| Which specific devices it can be associated with | | |
| Material(s) used | | |
| Uses/functions/applications | | |

Referring to FIG. 3C there are depicted first to fourth images 3000A through 3000D of a wireless user assembly according to an exemplary embodiment of the invention, displaying a design not present in the prior art that is itself an aspect of the invention. As depicted in first image 3000A the wireless user assembly comprises an EEG sensor 3030, earpiece 3035, and body 3040. Referring to second image 3000B the earpiece 3035 is coupled to the body 3040 via first arm 3020 which provides in conjunction with the body 3040 the structure that rests upon the user's upper portion of the ear thereby supporting the wireless user assembly when worn by the user. The EEG sensor 3030 is coupled to the body 3040 via flexible arm 3010 allowing the EEG sensor 3030 to be positioned against the user's head. Second arm 3050 provides additional engagement against the user's ear close to the joint of the ear to the head whilst the thicker body 3040 sits away from their ear providing improved comfort. It would be evident that with a wireless interface within the body 3040, the user assembly can communicate EEG data with a user's PED/FED, as well as receive wireless audio signals given to the user via earpiece 3035.

Optionally, a microphone may be included in the wireless assembly, allowing it to concurrently act as both portable EEG device and wireless hands free headset for use with a PED or FED. The microphone could be positioned in numerous locations, such as behind the ear attached to body 3040 at position 3062 or inside the body 3040 sitting below the user's ear, with the microphone facing forward and receiving sound through a slit (or series of slits) at position 3061. Optionally (and ideally), the body 3040 may be small enough to fit behind the user's ear, providing a more discrete user assembly. Similarly, an EEG sensor embedded within the body of the user assembly would provide further footprint reduction, i.e. cover less of a user's head) and discrete provisioning of an EEG sensor within a wireless user assembly.

Figure 4:
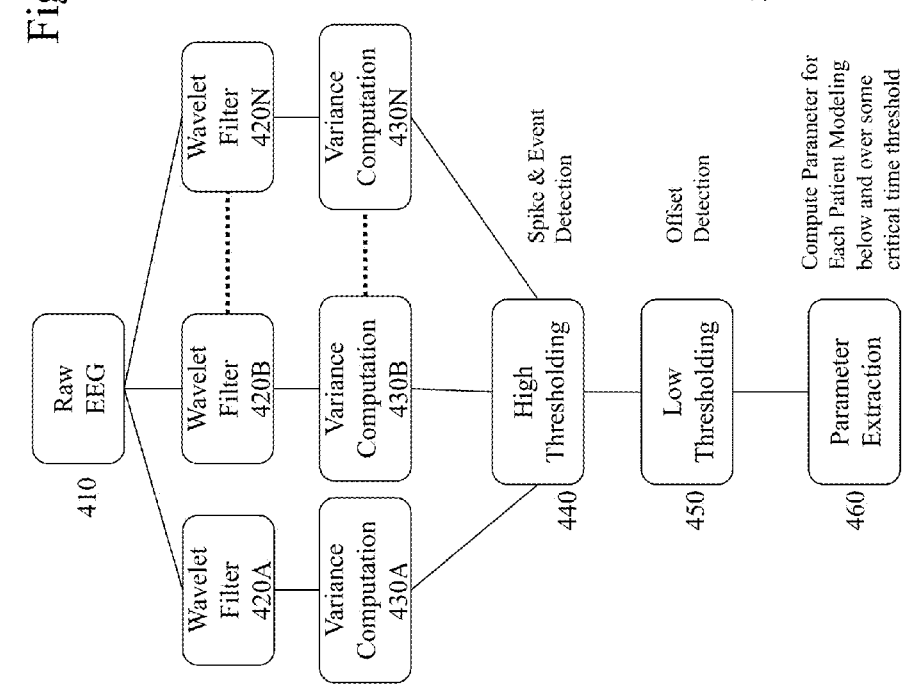
FIG. 4 depicts an exemplary process flow for processing EEG signal(s)

Now referring to FIG. 4 there is depicted an exemplary flow chart for signal processing of EEG data according to an embodiment of the invention. As depicted in first step 410 raw EEG data is received from an EEG sensor via intermediate circuitry, e.g. a low leakage ESD proof structure and analog-to-digital converter (ADC), wherein the EEG data is then structured into a series of 1-second long data sequences clumped into a discrete "packet" of data in an exemplary embodiment of the invention, with each packet containing up to 1000 raw EEG voltage value samples. The length of and number of samples within each sequence may vary in other embodiments. Each packet is coupled to a plurality of Wavelet Filters 420A through 420N for processing, whereby each of the different Wavelet Filters 420A through 420N applies a different process to the packet (each extracts a different wavelet). The processed outputs from the plurality of Wavelet Filters 430A through 430N are then coupled to a plurality of Variance Computation blocks 430A through 430N (respectively, where 420A couples to 430A, 420B couples to 430B, and so on) which generate statistical data relating to each processed 1-second long sequence of EEG data (packet) in order to calculate, for example, the variance of each packet. The variance results for the current 1-second sequence and the raw EEG data within the packet are simultaneously forwarded from all Variance Computation blocks 430A through 430N, to High Thresholding 440, wherein spikes and/or events are identified. The processed EEG data is then processed by Low Thresholding block 450 in order to remove offsets within the data and then this is coupled to Parameter Extraction block 460 wherein parameters for the user are derived from modeling analysis according to one or different time periods including any determined critical time thresholds.

It would be evident that removal of artifacts, e.g. muscle movement, from EEG data can be accomplished via other methodologies besides the aforementioned wavelet transform-based analysis paradigms. Artifacts can also be removed using, for example, empirical mode decomposition, canonical correlation analysis, independent component analysis, or some combination of methodologies. Furthermore, learning algorithms such as support vector machines and multilayer perceptrons can be employed for greater accuracy albeit slower and with more complex processing. As such, aspects of FIG. 4 relating to artifact removal merely represent (parts of) an exemplary process of artifact removal and furthermore, since many variants of wavelet transform filtering exist and can be employed to this end, it is also merely an example of one exemplary method of using wavelet transforms to remove artifacts.

Figure 5:
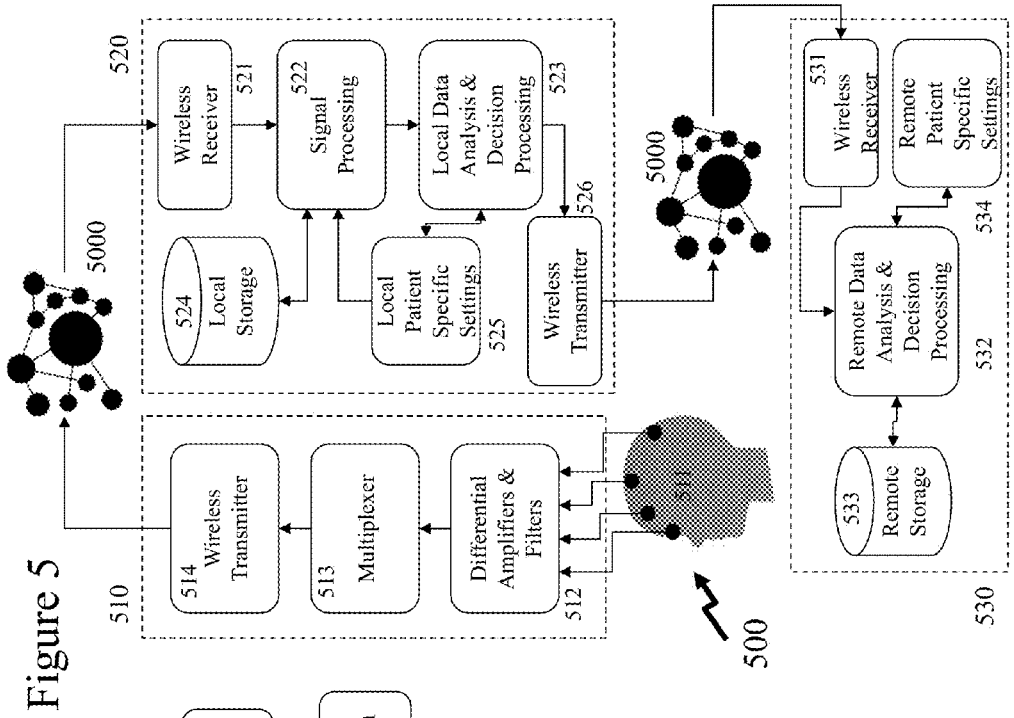
FIG. 5 depicts an exemplary EEG system configuration according to an embodiment of the invention comprising EEG embedded headset, local EEG processing module, and remote EEG processing module.

Now referring to FIG. 5 there is depicted a functional schematic for a distributed neurological data acquisition system (DNAS) 500 according to an embodiment of the invention. DNAS 500 in this example is another exemplary system for processing EEG data. DNAS 500 is comprised of a Data Acquisition Unit (DAU) 510, a Local Data Processing Module (LDPM) 520, which may be for example a user's PED, and a Remote Data Processing Module (RDPM) 530, e.g. a server accessible through the internet. Electrodes 511 detect analog signals (voltage readings) generated by electrical-neurological activity in the brain of the user, i.e. EEG signals. The electrodes 511 are coupled to Differential Amplifiers/Filters 512 which are part of DAU 510 and increase the magnitude of the electrical signal detected by the electrodes 511 whilst filtering out/discarding voltage readings that are too high or low to have been produced by brain activity. These pre-processed EEG signals are then coupled via a Multiplexer 513 to a first Wireless Transmitter 514, wherein they are transmitted via Network 5000 to the LDPM 520 and first Wireless Receiver 521. The output from the first Wireless Receiver 521 is coupled to Signal Processing 522 which also receives input from Local Storage 524 and Local User Specific Settings 525. The processed output from the Signal Processing 522 is then coupled to Local Data Analysis & Decision Processing 523 which also receives data from the Local User Specific Settings 525. The processed output from the Local Data Analysis & Decision Processing 523 is then coupled to second Wireless Transmitter 526, which transmits the processed data through network 5000 to RDPM 530, where it is received by second Wireless Receiver 531. The processed output from LDPM 520 is then further processed by the series of algorithms present in the Remote Data Analysis & Decision Processing 532 module in conjunction with a module storing information about the user and their selected settings (Remote User Specific Settings 534), as well as data retrieved from Remote Storage 533. Once these analyses are complete, the processed data is fed to a directed input of a software application/software system/machine interface (SASSMI)—often associated with LDPM 520 (and often involving transmitting the data back to LDPM 520 and sometimes to a separate SASSMI)—wherein the processed EEG data is employed in an action such as (but not limited to) controlling a system, controlling a machine, establishing a decision, triggering a medical event (e.g. a warning for an impending seizure), triggering a response, directly displaying information in real-time about the user's mental activity (especially if the user is performing a neurofeedback exercise), and modifying at least one of the user-specific data stored within the local or remote setting databases, e.g. Local User Specific Settings 525 and/or Remote User Specific Settings 534. This data can also be stored in the SASSMI and/or LDPM 520 for later use—e.g. to display the data to the user on a "history screen" through which the user can track their changes in mental activity over time—especially in relation to metrics generated from mental activity such anxiety level.

According to an embodiment of the invention a user may have multiple User Assemblies, e.g. DAU 510, such as for example an earpiece, Bluetooth headset, motor bicycle crash helmet, a safety headset at work, etc. Each may have at least an EEG sensor and an EEG reference sensor and accordingly, each may associate with the user's PED (or PEDs, if the user has associated the device with more than one) during their use of each, with a calibration routine switching which user assembly is currently connected to the PED each time the user switches which user assembly they are wearing (e.g. when the user removes their motorcycle helmet and puts on their Bluetooth headset). Accordingly, the User Assembly currently in use provides EEG data to the PED for processing and/or classification plus coupling to the remote systems and/or applications. Hence, applications of embodiments of the invention allow for multiple User Assemblies to be used and the retrieved EEG data to be processed and pushed to the remote storage. Optionally, multiple PEDs and FEDs may be associated to the user such that their EEG data acquisition continues as they e.g. walk around their work or home, drive their car, etc. wearing different User Assemblies. Additionally, each User Assembly, e.g. DAU 510, may contain memory for storing a predetermined duration of data to allow for handovers, failures, communication outages etc. If the User Assembly is out of communication for more than the predetermined duration of time for which EEG data can be stored then the User Assembly may exploit a first-in first-out methodology and simply keep the latest data. In other instances where some pre-processing is performed within the User Assembly then data relating to initially assessed events may be preferentially stored. In other embodiments of the invention, the need for procedures that switch which User Assembly is connected to the PED (or PEDS and/or FEDs) may not be present, such as through the use of a more versatile form of the User Assembly that can be worn/used in a larger variety of contexts (IE fits under a wide variety of different forms of headwear and/or can be continuously worn inconspicuously without the presence of headwear, thus eliminating the need for multiple user assemblies).

Accordingly, biomedical data, in this instance EEG data received from the EEG sensors, e.g. electrodes 511, may be processed locally (i.e. in close proximity to the DAU 510) by the LDPM 520, remotely by the RDPM 530, or in both the LDPM 520 and RDPM 530, with different analyses occurring in each. Accordingly, the DAU 510 with DNAS 500 is assumed to simple provide EEG signal conditioning and hence LDPM 520 and RDPM 530 may apply one or more processes relating to analyzing and/or determining EEG signals including but not limited to K-nearest neighbour algorithms, K-means algorithms, support vector machines, support vector networks, relevance vector machines, relevance vector networks, multilayer perceptron neural networks, neural networks, single layer perceptron models, logistic regression, logistic classifiers, decision trees, Bayesian linear classifiers, naïve Bayes, fuzzy entropy, fuzzy logic, linear discriminant analysis, linear regression, signal space projections, hidden Markov models, and ensemble classifiers including but not limited to bagging, random forests, random subspaces, bootstrapping aggregating, and AdaBoost.M1. More complex analyses would generally be conducted by the RDPM 530, with less processor intensive analyses/classification methods conducted by the LDPM 520.

Figure 6:
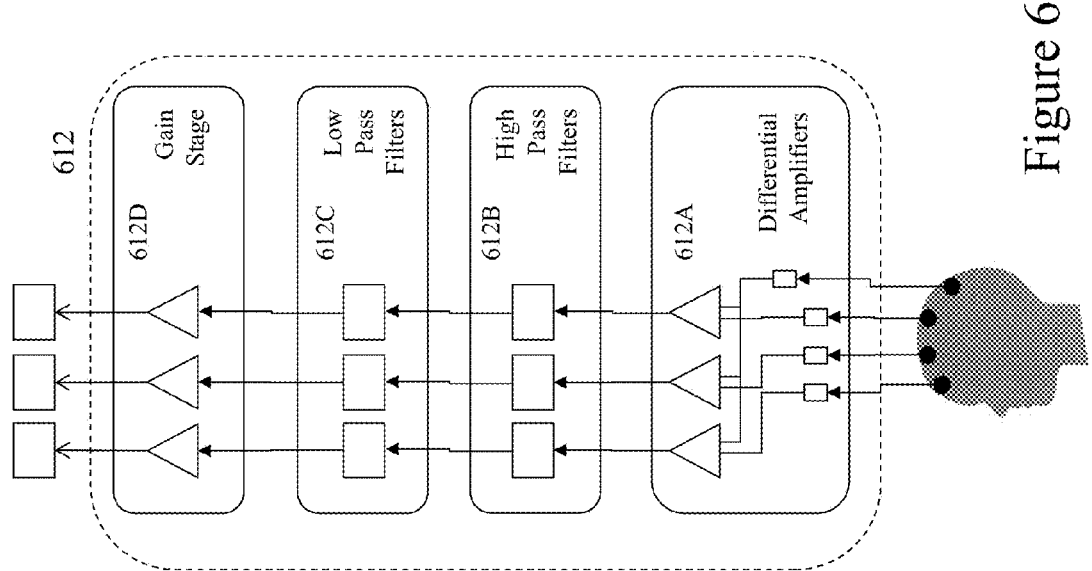
FIG. 6 depicts an exemplary EEG signal amplification/filter block for use within an EEG embedded headset according to an embodiment of the invention.

Now referring to FIG. 6 there is depicted a functional layout of an exemplary sensor interface circuit, e.g. Differential Amplifier and Filter (DAF) stage 512 within DAU 510 of FIG. 5. As depicted multiple signals from sensors, e.g. electrodes 611, are received by a plurality of Operational Amplifiers (OpAmps) 612A wherein the output of the plurality of OpAmps are then passed through High Pass Filters 612B and Low Pass Filters 612C, followed by more amplifiers in Gain Stage 612D. The amplifiers in Gain Stage 612D may for example be low ESD leakage structures such as described in respect of FIG. 4 with unitary gain, the amplification circuit depicted in FIG. 1D, or another amplification circuit supporting low noise, low frequency amplification of electrical signals.

Figure 3B:
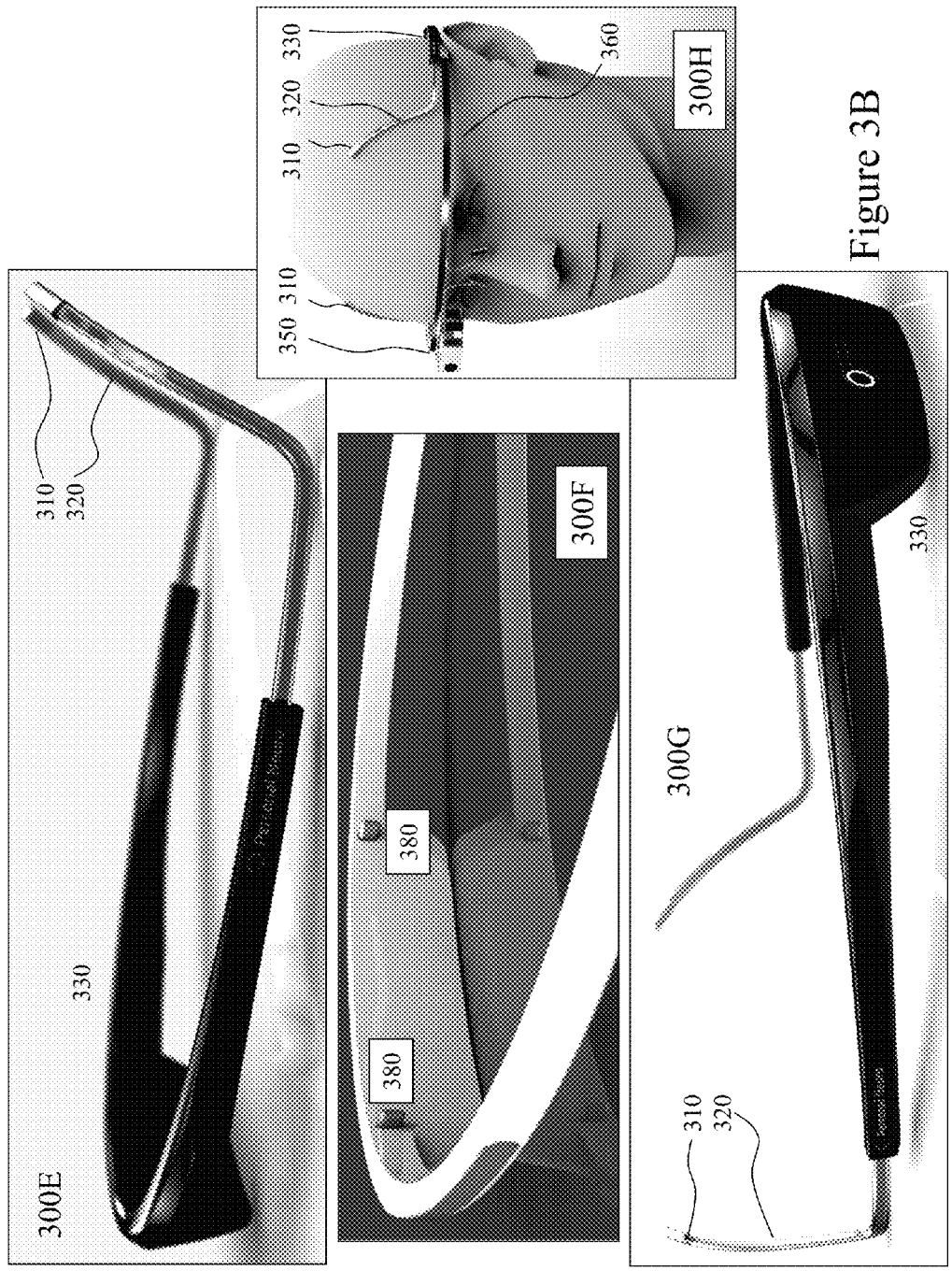

Within the description supra in respect of FIGS. 3A and 3B for the EEG headset 330 according to an embodiment of the invention a design using four EEG sensors, these being a pair of EEG sensors 310 and a pair of EEG contacts 380. Historically, as discussed supra EEG headsets fall into 2 categories, namely those for medical/research applications with a large number of sensors; and simple devices with a small number of electrodes geared towards consumer devices and applications e.g. games and general health and wellness software. However, the inventors wished to establish with their EEG headset 330 a device capable of supporting a wide range of EEG based analysis, metric determination, etc. to support a wider range of applications.

Figure 7:
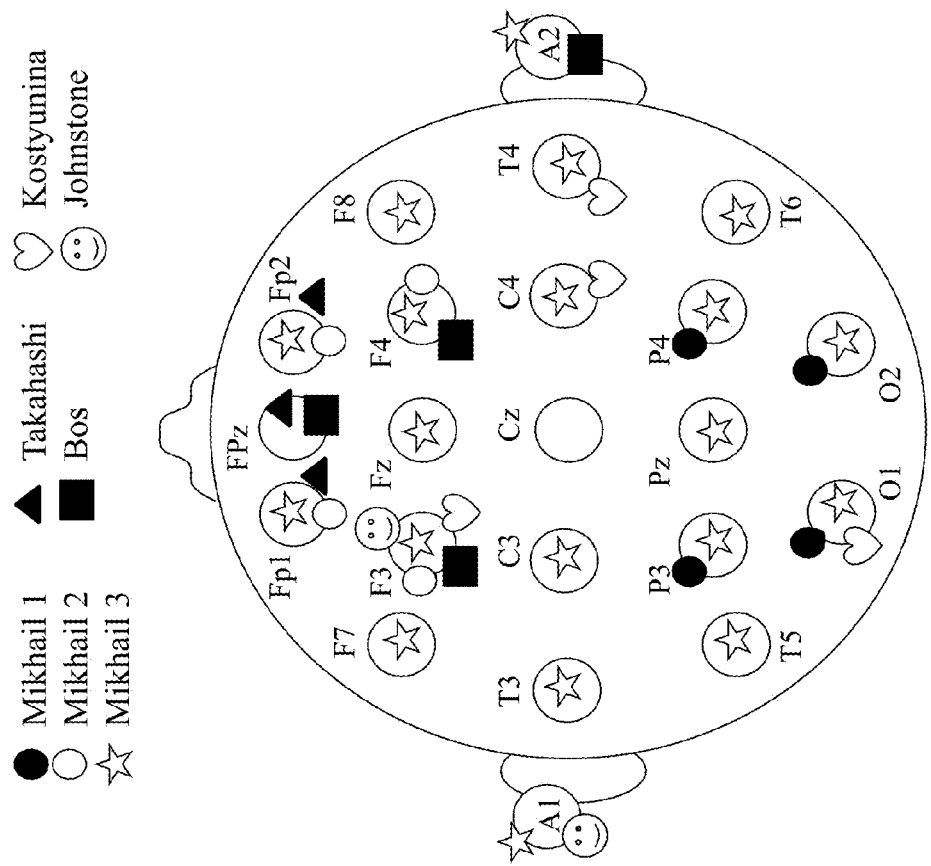
FIG. 7 depicts a mapping of EEG sensor locations from prior art research for minimal electrodes.

Within the prior art work on what may be termed, minimal electrode placements, includes Bos et al. in "EEG-based Emotion Recognition—The Influence of Visual and Auditory Stimuli" (Technical Report, pp. 1-17, 2006); Johnstone et al. in "EEG From a Single-Channel Dry-Sensor Recording Device" (Clin EEG Neurosci, Vol. 43(2), pp. 112-120); Kostyunina et al. in "Frequency Characteristics of EEG Spectra in the Emotions" (Neurosci. & Behav. Physio., Vol. 26(4), pp. 340-3); Mikhail et al in "Using Minimal Number of Electrodes for Emotion Detection using Brain Signals Produced from a New Elicitation Technique" (Int. J. Autonomous and Adaptive Communications Systems, Vol. 6(1), pp. 80-97); and Takahashi in "Remarks on Emotion Recognition from Bio-Potential Signals" (Interface, pp. 186-191). The placement of the electrodes within these prior art experiments are depicted in FIG. 7 with respect to a view from above a user's head showing the conventional labelling of nodes together with the node configurations employed by Mikhail, Takahashi, Bos, Kostyunina, and Johnstone together with a essentially a research configuration of Mikhail. Within these prior art trials then primarily research has focused to frontal lobe measurements, e.g. Takahashi exploits FP1, FP2, and FPz; Mikhail exploits F3, F4, FP1, and FP2; and Box exploits F3, F4, FPz, and A2. Some research has addressed occipital lobe measurements, e.g. Mikhail exploited O3, O4, P3, and P4 in a second setup whereas Kostyunina exploited O1, F3, C4, and T4. Generally reference electrode positions have been at one or both ears, i.e. A1 and/or A2.

Figure 8:
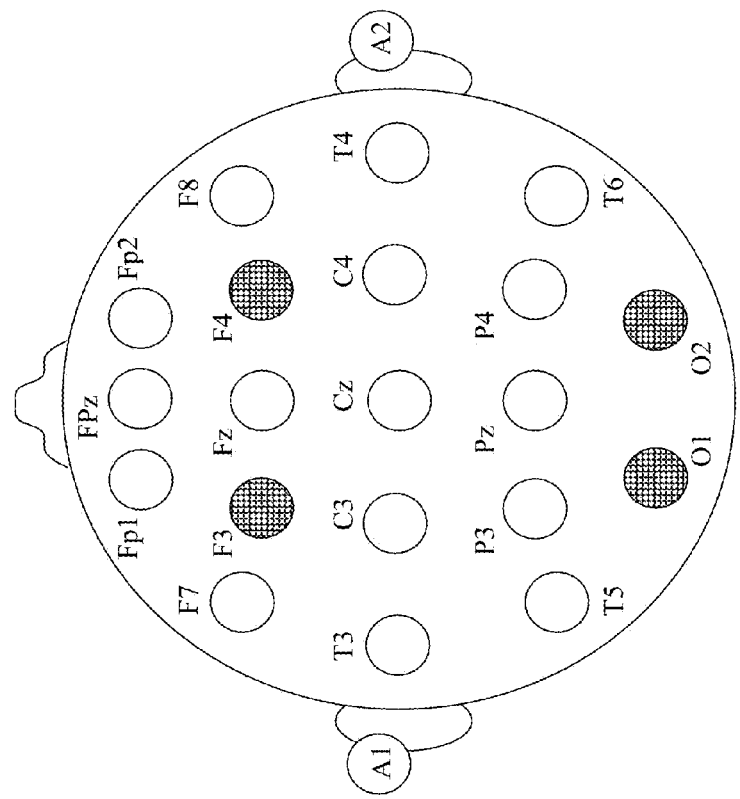
FIG. 8 depicts the EEG sensor locations of an EEG headset according to an embodiment of the invention for minimal electrodes and high user acceptability.

However, based upon analysis and experimentation the inventors have been able to establish that exploiting O1, O2, F3 and F4 as depicted in FIG. 8 provides sufficiently accurate data for analysis with their processing algorithms. Beneficially this allows the design and implementation of the EEG headset 330 with a rear headband design removing many of the issues for users of EEG wearable devices in respect of their visibility to others and their impacting the user's ability to exploit a HMD such as Google Glass™ as well as wear/place/remove hats etc. Optionally, additional sensors within the EEG headset 330 may include T5, T3, T4, and T6. Optionally, a further sensor or sensors in addition to O1, O2, F3 and F4 may be attained by adding an EEG sensor to the HMD 360 just above the bridge of the nose thereby adding FPz and/or Nz node measurements. As the HMB 360 and EEG headset 330 both exploit WPAN/short range wireless communications their data may be merged upon the user's PED for example or communicated from HMD 360 to EEG headset 330 for initial processing and communication with a PED and/or FED associated with the EEG headset 330.

Now referring to FIG. 9 there are depicted first to sixth EEG traces 910 to 960 taken over an approximately 10 second period, generally in relation to sleep. These being:

Awake 910 which is characterized by low voltage, random, and fast EEG variations. This doesn't represent a person's only awake state, merely an example of one, which is primarily comprised of beta and alpha waves, with a small influence from gamma. It could also be described as an "alert" state;

Drowsy 920, dominated by periodic 8-12 Hz alpha waves—generally seen in states in which a person is tired, though it can also appear in states of relaxation where the subject does not report drowsiness;

Stage 1 Sleep 930—dominated by 3-7 Hz theta waves;

Stage 2 Sleep 940—dominated by 12-14 Hz waves, with sleep spindles 941 and K-complexes 942 occurring at seemingly random (though not truly random) intervals;

Delta Sleep 950, also known as stage 4 sleep or "deep sleep". This is difficult to differentiate from stage 3 sleep, which is frequently described as merely a transitional phase between "light sleep" (stage 2 sleep 940) and deep sleep 950 rather than a discrete stage of sleep in and of itself. As such, the more readily distinguishable stage 4 sleep 950 is displayed here. 0.5-2.0 Hz delta waves predominate during delta sleep 950, but as with all stages, do not account for all variation in the EEG wave;

REM Sleep 960 which is primarily composed of low voltage, seemingly (but not truly) random waves of comparatively high frequency in comparison to other stages of sleep. EEG waves present in REM sleep 960 have a greater resemblance to waves seen in awake states (e.g. Awake 910), but contain unique and distinctive saw tooth waveform segments 961 not generally seen a person's waking EEG.

Figure 10B:
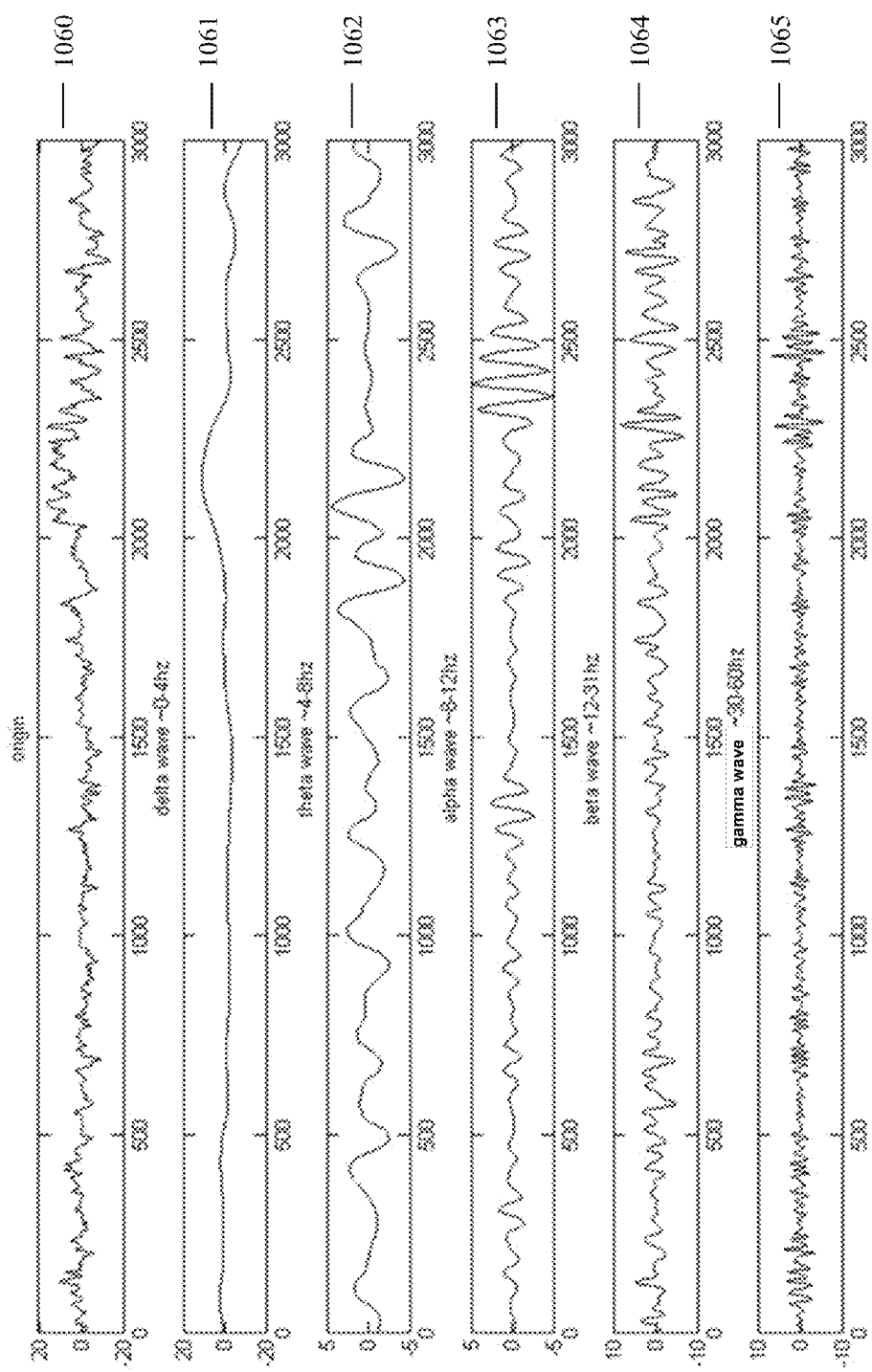

EEG can be broken down into its frequency spectra via Discrete Fourier transforms (e.g. FFTs), which are used to categorize the waves into frequency bands. Though there is variance in which frequency bands are selected and which ranges chosen for each, there are typical spectral regions within which each band is placed. An exemplary and fairly typical set of selected wave bands and the frequencies chosen for each band are depicted in FIG. 10B, wherein the raw EEG band 1060 is broken down into delta waves 1061 from 0-4Hz, theta waves 1062 from 4-8Hz, alpha waves 1063 from 8-12Hz, beta waves 1064 from 12-31Hz, and gamma waves 1065 from 30-60Hz. Other embodiments choose other wave bands, and ranges for wave bands. Some embodiments break certain wave bands down into sub-bands, such as alpha1 from e.g. 8-10Hz and alpha2 from e.g. 10-12Hz. A more in-depth Now referring to FIG. 10 there is depicted an exemplary EEG spectrum 1000, depicting an example of how the power within a user's EEG can vary. The spectra depicted in 1000 are fairly typical, but vary considerably between users/subjects dependent on numerous factors including (but not limited to) age, the presence of neurological disorders, and the activity the user is engaged in. The exemplary band definitions for EEG spectra are presented below together with mental/neurological/psychology states roughly connected to changes in each band, along with pathologies roughly associated with abnormalities in each band.

Delta—0 Hz to 4 Hz: Normally associated with deep sleep (NREM stages 3 and 4 and certain continuous attention tasks (less well-accepted). Pathologies associated with abnormalities in this band include increased frequency in waking states in brain injury and brain tumour patients, increased in waking states in schizophrenia patients, and reduced levels during sleep are associated with low-quality sleep and disorders that cause low-quality sleep (such as major depression).

Theta—4 Hz to 8 Hz: Normally associated with sleep (NREM stages 1 and 2), drowsy states when awake, active suppression of thoughts and behaviours previously elicited by stimuli, and meditation. Pathologies associated with abnormalities in this band include hydrocephalus, focal brain lesions, and increased in ADHD.

Mu—8 Hz to 13 Hz (directly over the sensori-motor cortex): Normally associated with observation of behaviour in other people, suppressed when performing or visualizing motor activities, and increased before and after motor activities. Pathologies associated with abnormalities in this band include autism.

Alpha—8 Hz to 14 Hz: Normally associated with relaxation, behaviour inhibition, closed-eye resting state, rumination and self-reflection, and meditation. Pathologies associated with abnormalities in this band include coma.

Beta—14 Hz to ~40 Hz: Normally associated with normal waking consciousness with eyes-open, visual attention, active concentration, anxiety/nervousness, voluntary suppression of movement, and alertness together with maintenance of current behaviour. Pathologies associated with abnormalities in this band include reduction in ADHD and increased in generalized anxiety disorder.

Gamma—~40 Hz to ~100 Hz: Normally associated with combining sensory information from multiple senses, reasoning, creative and abstract thinking, and short-term memory tasks involving matching stimuli with existing memories together with switching between behaviours. Pathologies associated with abnormalities in this band include increased frequency associated with cognitive decline.

Insert 1050 in FIG. 10A zooms in on a segment of EEG spectrum 1000 to depict a common power spike observed in EEG spectra known as the peak alpha frequency which describes an often-occurring sudden increase and immediately subsequent rapid drop in spectral power appearing approximately one-third of the way through a user's alpha frequency band. Peak alpha frequency 1050 is a particularly important phenomenon because it can be used to calibrate the frequency ranges of each band to be specific to each user peak. This is possible because the peak alpha frequency 1050 almost always occurs ⅓ of the way through the alpha band, most bands including the alpha band have approximately the same width in most users, and bands are always positioned in a specific order. Certain embodiments of the invention take advantage of peak alpha frequency 1050 to calculate frequency band ranges for individual users to better determine their mental states—as opposed to the use of predefined frequency band ranges as utilized in other embodiments. Note that in other embodiments other features of a user's EEG can be used instead of peak alpha frequency 1050 to calibrate a user's frequency band ranges. Furthermore, other embodiments may use other features in tandem with peak alpha frequency 1050 to more accurately and/or precisely define a user's frequency band ranges. Such methods are a major aspect of a now commonly-used set of EEG methodologies known as "quantitative EEG" (qEEG) that use quantitatively determined rather than semi-arbitrarily pre-defined frequency band ranges. qEEG, variants of various qEEG methods, or certain aspects of qEEG may be utilized by certain embodiments of the invention.

Figure 11:
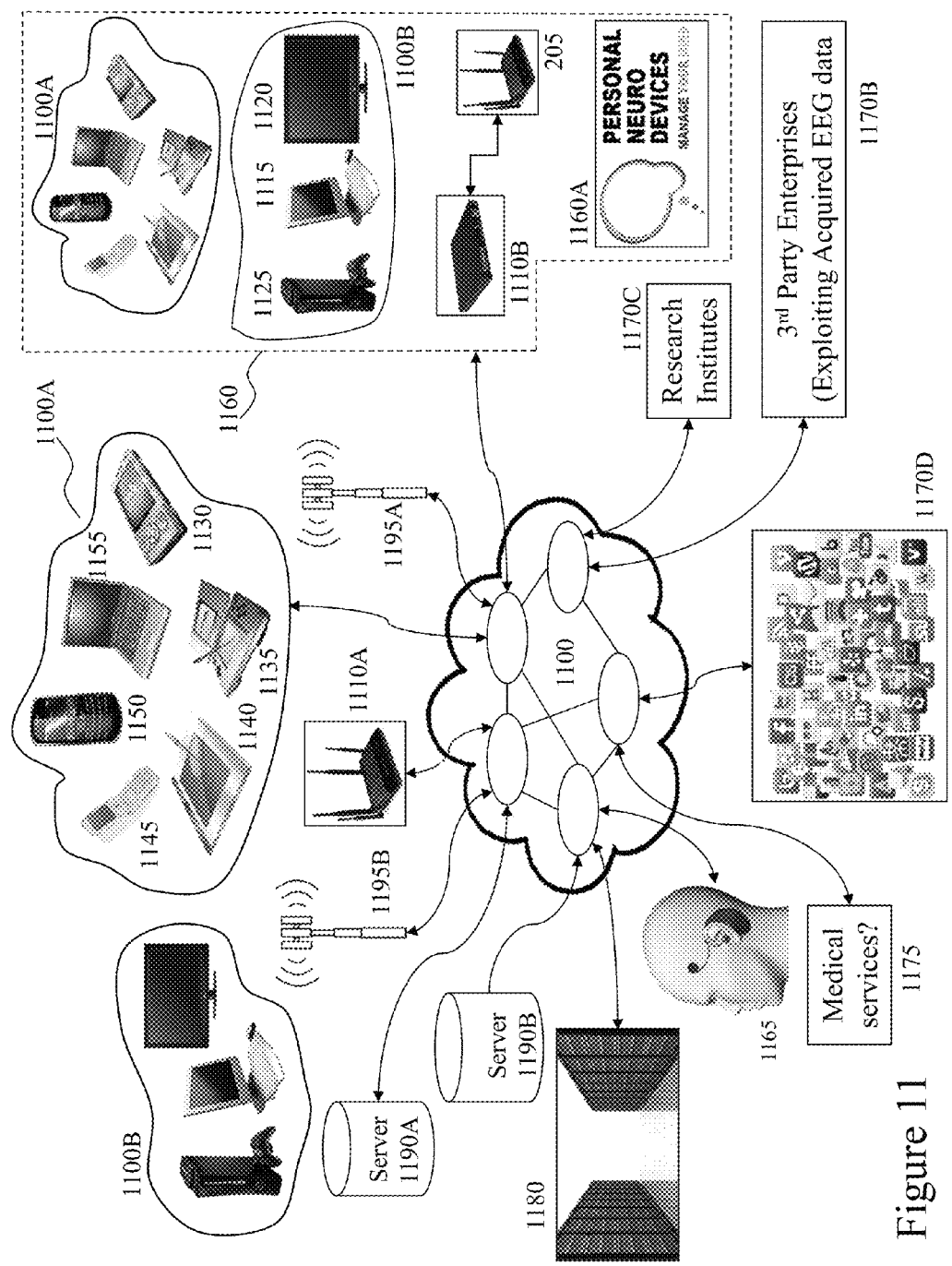
FIG. 11 depicts a communications network supporting communications with EEG embedded headsets, local EEG processing module, and remote EEG processing modules according to an embodiment of the invention.

Now referring to FIG. 11 there is depicted a network 1100 supporting communications to and from electronic devices according to an embodiment of the invention wherein EEG waveform data for an individual may be transferred online remote processing elements, e.g. remote servers, server farms, data centers, etc., further deeper analysis using increased online computing resources, i.e. cloud computing, storage, and optionally sharing user EEG data/EEG analysis results/user mental states via one or more formats including, but not limited to, social media, social network(s), email, short message services (SMS), blogs, posts, etc. As shown, first and second user groups 1100A and 1100B interface to a telecommunications network 1100. Within the representative telecommunication architecture a remote central exchange 1180 communicates with the remainder of a telecommunication service providers network via the network 1100 which may include for example long-haul OC-48/OC-192 backbone elements, an OC-48 wide area network (WAN), a Passive Optical Network, and/or a Wireless Link. The central exchange 1180 is connected via the network 1100 to local, regional, and international exchanges (not shown for clarity) and therein through network 1100 to first and second wireless access points (AP) 1195A and 1195B which provide Wi-Fi cells for first and second user groups 1100A and 1100B respectively. Also connected to the network 1100 are first and second Wi-Fi nodes 1110A and 1110B, the latter of which is coupled to network 1100 via router 1105. Second Wi-Fi node 1110B is associated with Enterprise 1160A, in this instance Personal Neuro Devices Inc. (a provider of User Assemblies and software applications exploiting EEG biosignals), and environment 1160 within which are first and second user groups 1100A and 1100B. Second user group 1100B may also be connected to the network 1100 via wired interfaces including, but not limited to, DSL, Dial-Up, DOCSIS, Ethernet, G.hn, ISDN, MoCA, PON, and Power line communication (PLC) which may or may not be routed through a router such as router 1105.

Within the cell associated with first AP 1110A in FIG. 11 the first group of users 1100A may employ a variety of portable electronic devices (PEDs) including for example, laptop computers 1155, portable gaming consoles 1135, tablet computers 1140, smartphones/superphones 1150, cellular telephones/cellphones 1145, and portable multimedia players 1130. Within the cell associated with second AP 1110B are the second group of users 1100B who may employ a variety of fixed electronic devices (FEDs) including for example gaming consoles 1125, personal computers 1115, wireless/Internet-enabled televisions 1120, and cable modems 1105. Also connected to the network 1100 are first and second APs which provide, for example, cellular GSM (Global System for Mobile Communications) telephony services as well as 3G and 4G evolved services with enhanced data transport support. Second AP 1195B provides coverage in the exemplary embodiment to first and second user groups 1100A and 1100B. Alternatively the first and second user groups 1100A and 1100B may be geographically disparate and access the network 1100 through multiple APs, not shown for clarity, distributed geographically by the network operator or operators. First AP 1195A as show provides coverage to first user group 1100A and environment 1160, which comprises second user group 1100B as well as first user group 1100A. Accordingly, the first and second user groups 1100A and 1100B may according to their particular communications interfaces communicate to the network 1100 through one or more wireless communications standards such as, for example, IEEE 802.11, IEEE 802.15, IEEE 802.16, IEEE 802.20, UMTS, GSM 850, GSM 900, GSM 1800, GSM 1900, GPRS, ITU-R 5.28, ITU-R 5.150, ITU-R 5.280, and IMT-2000. It would be evident to one skilled in the art that many portable and fixed electronic devices (PEDs and FEDs, respectively) may support multiple wireless protocols simultaneously, such that for example a user may employ GSM services such as telephony and SMS, Wi-Fi/WiMAX data transmission, VoIP, Internet access etc. Accordingly portable electronic devices within first user group 1100A may form associations either through standards such as IEEE 802.15 and Bluetooth, and/or in an ad-hoc manner.

Accordingly, any of the PEDs and/or FEDs may provide and/or support the functionality of a local biosensor processing unit (LBPU), such as LDPM 620 in FIG. 6 for example, to process and/or store biosignals acquired from a User Assembly (mainly EEG signals, but in some embodiments not exclusively EEG signals) such as depicted supra in respect of User Assembly 310 in FIG. 3A or first to third User Assemblies 3000A to 3000C respectively in FIG. 3B for example as processed and transmitted by a Data Acquisition Unit (DAU) e.g. DAU 610 in FIG. 6. Accordingly, such LDPUs may receive biosignals—mainly EEG signals (i.e. scalp voltage recordings) but in some embodiments not exclusively EEG signals—and perform localized storage, processing, etc. on these signals. In some embodiments of the invention the PEDs/FEDs may also provide the required functionality of the DAU in addition to that of a LBPU.

Further, as depicted first and second servers 1190A and 1190B respectively which are connected to network 1100 and accordingly can receive communications from any PED/FED within first and second user groups 1100A and 1100B respectively as well as other PED/FED devices connected to the network 1100. Accordingly, the first and second network servers 1190A and 1190B may support the functionality discussed supra in respect of a remote biosignal processing unit (RBPU) such as a RDPM 530 presented supra in respect of FIG. 5 such that additional processing and/or storage may be supported. Within another embodiment of the invention the User Assembly, depicted as User Assembly 1165 in FIG. 11, may be remotely connected to the LBPU and/or LDPM through a wireless interface other than a local area network interface such as Bluetooth for example such that data communications may be undertaken over a larger area and in the event of a lost or misplaced PED for example. Optionally the User Assembly may include local and network wireless interfaces and select which to employ based upon the automatic association or lack of association with the user's PED and/or FED.

External servers connected to network 1100 include servers belonging to research institutes 1170C for analyzing our data for scientific purposes. Such purposes can include, but are not limited to, finding information for treating mental disorders, discovering new ways to filter EEG data to get a less noisy signal, and developing algorithms that detect new mental states. Outside servers also include medical services 1175, which can use the data for such purposes as tracking neurological events like seizures or notifying doctors and emergency services in the event of serious events like heart attacks and strokes that have an impact on brain activity. Third party servers 1170B also connect to our network for purposes like e.g. determining ads that are more likely to be of interest to a particular user based on their EEG activity, or associating emotions derived from EEG data with specific locations such as restaurants and theme parks.

Also connected to network 1100 are social networks 1170D such as Facebook™, Twitter™, LinkedIn™, Instagram™, Pinterest™, Yelp™ and Reddit™ for example. These may also be connected to first and second servers 1190A and 1190B respectively for example to acquire abstractions derived from EEG data of a registered user of one or more of the social networks 1170 or it may obtain data from User Assembly 1165 as well as the RBPU and/or RDPM for example. Accordingly, a registered user of an associated social network or social networks 1170D may post information relating to their emotional state derived from the EEG waveform data, self-ratings provided by users, scores on "cognitive" tasks relating to emotions, and/or ERP reactions to presented stimuli (mainly emotional imagery such as affectively negative and positive images). Such information may be posted directly e.g. as an emoticon, or through a color coding or style tagging method, including those that are directly applied to the displayed webpage(s)/profile(s) of the user of a social network or social networks within 1170D for example. Optionally, the user may elect to include such colour coding, style tagging, and/or emoticons as part of communications made by the user such as posts, tweets, and alike, as well as in electronic communications outside the scope of social networking, such as email and SMS. In other embodiments the social networks 1170D provider may combine derived data for a plurality of users in association with a single topic, thread, re-tweet etc. to provide an averaged or weighted sentiment of the plurality of users such as anger, sadness, etc. in response to the topic in question.

It would be evident that first and second servers 1190A and 1190B respectively may securely store information relating to a user's biosignals, including but not limited to raw EEG data, processed EEG data, and EEG event determinations for at least one of a predetermined period of time, for all sampled data, and within predetermined periods prior to and after any determined event. In some instances the EEG data may be strictly time-locked to an event as is necessary for certain EEG paradigms such as those based on ERPs or it may be more loosely linked to the event e.g. by applying tags to individual segments of EEG data. Such tags indicating what "state" a user is or was in, such as walking, or indicating that a specific notable event had just passed, such as the elicitation of a startle response from the user). In other embodiments of the invention the data stored upon a remote server—such as first and second servers 1190A and 1190B respectively—may include, but not be limited to, data acquired from activities relating to gaming, mental training such as meditation, neurofeedback training, self-monitoring of mental states (e.g. mood, anxiety, attention, stress), and/or self-monitoring of neurological states (e.g. seizures, strokes).

According to other embodiments of the invention exploiting the user assemblies, PEDs, FEDs, DAUs, LPDMs, RDPMs, LBPUs, and RBPUS in various combinations, games, software upgrades, firmware upgrades, analysis algorithms etc. may be associated with enterprises and/or organizations associated with financial transactions in order for the user to access/acquire these. Accordingly, financial service providers who may be associated with financial transactions of registrants with enterprises may similarly access the network and user-associated devices to acquire credentials, verify credentials, and associate firmware versions, hardware identities, etc. These together with first and second servers 1190A and 1190B, which together with others not shown for clarity, may host according to embodiments of the inventions multiple services associated with a provider of the software operating system(s) and/or software application(s) associated with the electronic device(s), a provider of the electronic device, provider of one or more aspects of wired and/or wireless communications, event databases, registration databases, credential identification databases, license databases, customer databases, websites, and software applications for download to or access by PEDs and/or FEDs. First and second primary content sources 1190A and 1190B may also host, for example, other Internet services such as search engine(s), financial services, third party internet-based or internet-requiring applications.

Figure 12:
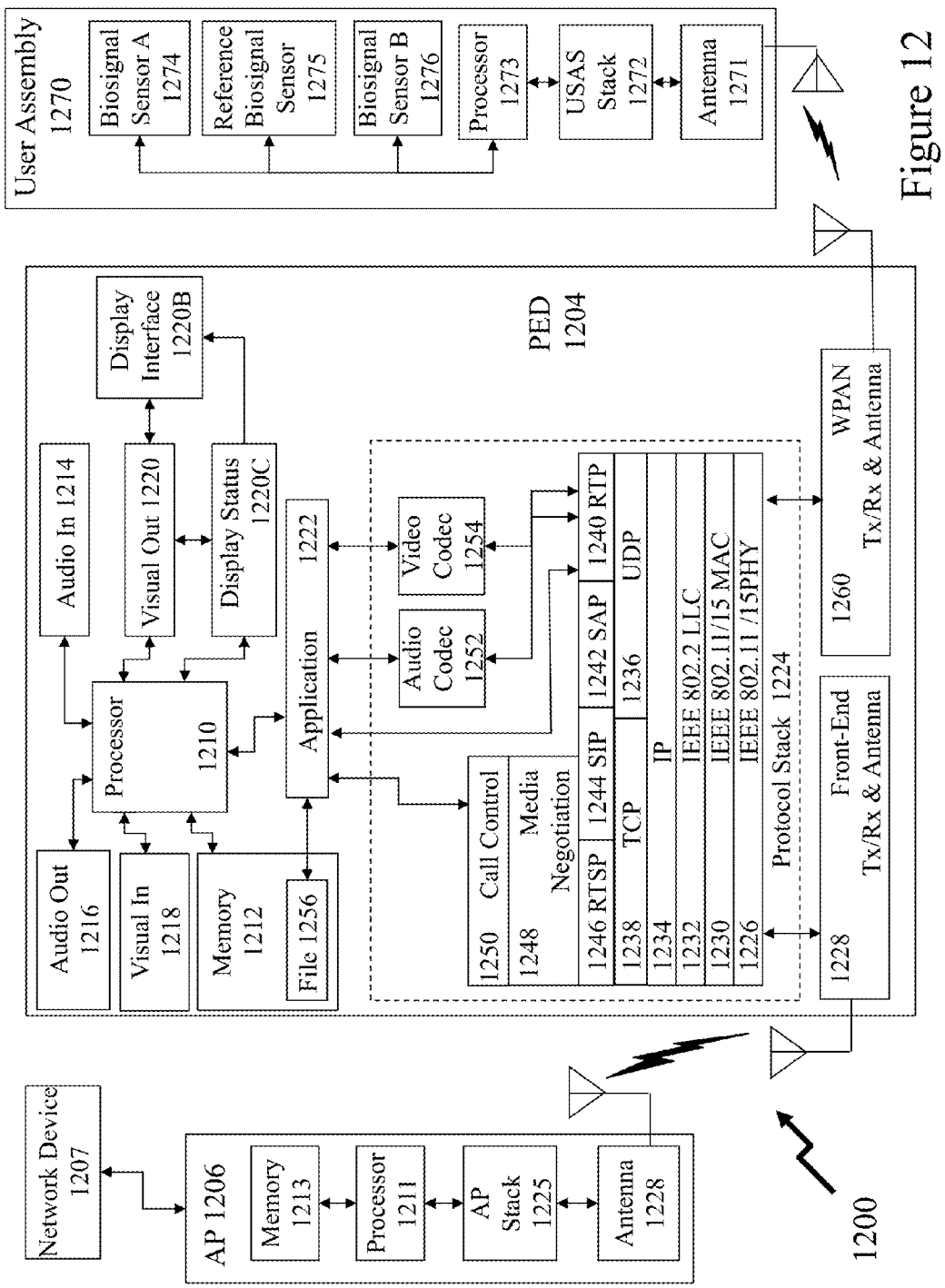
FIG. 12 depicts schematically the electronic elements of an EEG embedded headset, local EEG processing module upon a user's portable electronic device and ancillary network access point according to an embodiment of the invention.

Now referring to FIG. 12 there is depicted a PED 1204 supporting interfacing to a User Assembly (USAS) 1270 according to an embodiment of the invention such as described supra in respect of embodiments of the invention as well as the functions for a LBPU or LDPM, similarly described supra. Also depicted within the PED 1204 is the protocol architecture as part of a simplified functional diagram of a system 1200 that includes a portable electronic device (PED) 1204, such as a smartphone, an access point (AP) 1206, such as first Wi-Fi Access Point 1110, and one or more network devices 1207, such as communication servers, streaming media servers, and routers. Network devices 1207 may be coupled to AP 1206 via any combination of networks, wired, wireless and/or optical communication. The PED 1204 includes one or more processors 1210 and a memory 1212 coupled to processor(s) 1210. AP 1206 also includes one or more processors 1211 and a memory 1213 coupled to processor(s) 1211. A non-exhaustive list of examples for any of processors 1210 and 1211 includes a central processing unit (CPU), a digital signal processor (DSP), a reduced instruction set computer (RISC), a complex instruction set computer (CISC) and the like. Furthermore, any of processors 1210 and 1211 may be part of application specific integrated circuits (ASICs), Field Programmable Gate Arrays (FPGAs) or may be a part of application specific standard products (ASSPs). A non-exhaustive list of examples for memories 1212 and 1213 includes any combination of the following semiconductor devices such as registers, latches, ROM, EEPROM, flash memory devices, non-volatile random access memory devices (NVRAM), SDRAM, DRAM, double data rate (DDR) memory devices, SRAM, universal serial bus (USB) removable memory, and the like.

PED 1204 may include an audio input element 1214, for example a microphone, and an audio output element 1216, for example, a speaker, coupled to any of processors 1210. PED 1204 may include a video/visual input element 1218, for example, a digital camera, video camera, infrared sensor, or motion sensor; and a visual output element 1220, for example an LCD display, coupled to any of processors 1210. The visual output element 1220 is also coupled to display interface 1220B and display status 1220C. PED 1204 includes one or more applications 1222 that are typically stored in memory 1212 and are executable by any combination of processors 1210. PED 1204 includes a protocol stack 1224 and AP 1206 includes a communication stack 1225. Within system 1200 protocol stack 1224 is shown as IEEE 802.11/15 protocol stack but alternatively may exploit other protocol stacks such as an Internet Engineering Task Force (IETF) multimedia protocol stack for example. Likewise AP stack 1225 exploits a protocol stack but is not expanded for clarity. Elements of protocol stack 1224 and AP stack 1225 may be implemented in any combination of software, firmware and/or hardware. Protocol stack 1224 includes an IEEE 802.11/15-compatible PHY module 1226 that is coupled to one or more Front-End Tx/Rx & Antenna 1228, an IEEE 802.11/15-compatible MAC module 1230 coupled to an IEEE 802.2-compatible LLC module 1232. Protocol stack 1224 includes a network layer IP module 1234, a transport layer User Datagram Protocol (UDP) module 1236 and a transport layer Transmission Control Protocol (TCP) module 1238. Also shown is a wireless personal area network (WPAN) Tx/Rx & Antenna 1260, for example supporting IEEE 802.15.

Protocol stack 1224 also includes a session layer Real Time Transport Protocol (RTP) module 1240, a Session Announcement Protocol (SAP) module 1242, a Session Initiation Protocol (SIP) module 1244 and a Real Time Streaming Protocol (RTSP) module 1246. Protocol stack 1224 includes a presentation layer media negotiation module 1248, a call control module 1250, one or more audio codecs 1252 and one or more video codecs 1254. Applications 1222 may be able to create maintain and/or terminate communication sessions with any of devices 1207 by way of AP 1206. Typically, applications 1222 may activate any of the SAP, SIP, RTSP, media negotiation and call control modules for that purpose. Typically, information may propagate from the SAP, SIP, RTSP, media negotiation and call control modules to PHY (physical layer) module 1226 through TCP module 1238, IP module 1234, LLC module 1232 and MAC module 1230.

It would be apparent to one skilled in the art that elements of the PED 1204 may also be implemented within the AP 1206, including—but not limited to—one or more elements of the protocol stack 1224, including for example an IEEE 802.11-compatible PHY module, an IEEE 802.11-compatible MAC module, and an IEEE 802.2-compatible LLC module 1232. The AP 1206 may additionally include a network layer IP module, a transport layer User Datagram Protocol (UDP) module and a transport layer Transmission Control Protocol (TCP) module as well as a session layer Real Time Transport Protocol (RTP) module, a Session Announcement Protocol (SAP) module, a Session Initiation Protocol (SIP) module and a Real Time Streaming Protocol (RTSP) module, media negotiation module, and a call control module.

Also depicted is USAS 1270 which is coupled to the PED 1204 through a WPAN interface between Antenna 1271 and WPAN Tx/Rx & Antenna 1260. Antenna 1271 is connected to USAS Stack 1272 and therein to USAS Processor 1273. USAS Processor 1273 is coupled to Biosignal Sensor A 1274, Reference Biosignal Sensor 1275, and Biosignal Sensor B 1276 which can include, for example, electrodes for detecting data relating to one or more of EEG, EMG, EOG, etc. Furthermore, there can be further biosignal sensors besides those depicted. USAS 1270 being for example DAU 610 described above in respect of FIG. 6 with the addition of the USAS Processor 1273 and USAS Stack 1272. USAS 1270 may, for example, split processing with Processor 1210 within PED 1204 for processing functionality such that a lower power USAS Processor 1273 is deployed within USAS 1270, controlling acquisition of biosignal data from Biosignal Sensor A 1274, Reference Biosignal Sensor 1275, Biosignal Sensor B 1276, and any other biosignal sensors with instruction sets and some algorithms for example stored within the device's memory, not shown for the sake of clarity. It would be evident that data relating to the particular individual and/or biosignal characteristics for analysis defects may be stored within memory 1212 of PED 1204 and/or the memory of USAS 1270. Such data being stored within USAS 1270 when processing and/or pre-processing is performed by USAS 1270 rather than within PED 1204 and/or remote systems provided the data via AP 1206. This information may be remotely transferred to the PED 1204 and/or USAS 1270 from a remote system such as described above in respect of FIG. 11 via Network Device 1207 and AP 1206. Additionally, in software implemented filters or electronically controlled filters within a DAU, such as DAU 610 of FIG. 6 for example, such data may include the filter characteristics such as passband edge frequency, passband centre frequency, etc.

Accordingly it would be evident to one skilled the art that the USAS with associated PED may accordingly download original software and/or revisions (e.g. updates) for a variety of functions including diagnostics, EEG signal acquisition, EEG signal processing algorithms, etc. as well as revised user characteristic data relating to the individual's brain and/or other body regions for which biosignals are obtained. Accordingly, in certain embodiments a single generic USAS is manufactured then configured to the individual through software and user data, such that e.g. acquisition cycles, acquisition rates, processing, low pass filter characteristics, high pass filter characteristics, low pass filter characteristics, amplifier gain, etc. are calibrated to/customized for a specific user. Optionally, the elements of the PED required for network interfacing via a wireless network (where implemented), USAS interfacing through a WPAN protocol, processor, etc. may be implemented in certain embodiments in a discrete standalone PED as opposed to exploiting a consumer PED. A PED such as described in respect of FIG. 12 allows the user to adapt the algorithms employed through selection from internal memory, to define variants and in some instances control the operation of the USAS through for example a touchscreen, touchpad, keypad interface, externally connected keyboard, externally connected mouse, etc.

Accordingly, within the embodiments of the invention described supra various techniques, assemblies, algorithms, interfaces, and sensors have been described as examples of techniques for the detection, analysis, and response triggering of various physical, biological, physiological, and psychological/mental states of a human user (i.e. biosignals). Accordingly, techniques for providing various biosignal-based PED applications with capabilities that are more conducive to/allow long term monitoring and/or acquisition of biosignals, including but not limited to those detectable via ElectroCardioGraphy (ECG), ElectroEncephalography (EEG), ElectroMyoGraphy (EMG), ElectrOculoGraphy (EOG), Galvanic Skin Response (GSR), Body Temperature, Heart/Pulse Rate, fNIRS (functional near-infrared spectroscopy), non-EMG-based movement tracking, eye tracking/gaze detection, and other biosignals.

Various new and innovative applications can be provided that use enhanced interfaces for PEDs based on the detection and monitoring of various biosignals. For example, by integrating biosensors into the feature-rich environment of the PED, the addition of the user's physiological data gathered by the biosensor, in combination with the audio, multi-media, location, and/or movement data already collected by the PED provides a new platform for advanced user-aware interfaces and innovative applications. For example, a simulation environment intended to aid mental agility and/or skill development may adjust characteristics based upon the user's mental state. Similarly, a gaming environment might adapt to biosignals indicating fear, exhaustion, excitement, boredom, etc. by making the game easier if biosignals indicating frustration are detected, for example, or harder if excitement and concentration are detected. In some embodiments, a PED can include or be directed equipped with various biosensors or interfaces to various biosensors, e.g. biosignal sensors (capable of detecting biosignals) such as for detection/monitoring of one or more of for example the following: ECG, EEG, EMG, EOG, GSR, body temperature, heart/pulse rate, etc. For example, the user can either actively choose to interact with the biosignal sensors for a specific function or have the sensors passively detect/monitor certain biosignal information. This information may be stored on a user assembly with sensors, on a device associated with the user communicating with the user assembly, shared with other devices through a wired connection, shared with other devices through a wireless connection, or communicated to remote devices or services/applications over a network. Applications can then use this information for performing certain functions.

Certain embodiments of the invention as discussed supra are intended for use in establishing neurological events as well as the mental state of the user. By establishment of the appropriate algorithms and analysis routines mental states detected and classified for a user may include, but not be limited to, stress, relaxation, concentration, meditation, emotion and/or mood, valence (positiveness/negativeness of mood), arousal (intensity of mood), dominance (feeling of control present with the mood), anxiety, drowsiness, acute cognitive functioning (i.e. "mental fogginess" vs. "mental clarity"), sleep, sleep quality (for example based on time spent in each stage of sleep as easily detected with EEG), amount of time asleep, presence of a seizure, presence of seizure "prodromal stage" (indicative of an upcoming seizure), stroke detection, migraine presence, severity of migraine if migraine is present and prediction of impending migraine, heart rate, impending panic attack, and the presence of a panic attack. Biomarkers for numerous mental and neurological disorders—to e.g. aid in screening for said disorders—may also be established through biosignal detection and analysis. In addition, multiple disorders are expected to have detectable EEG biomarkers—or already have detectable EEG biomarkers—with increased EEG sample acquisition for a single user and increased user statistics/data. Such disorders may include, but are not limited to, depression, bipolar disorder (both type 1, type 2, and NOS), cyclothymia, generalized anxiety disorder, Alzheimer's disease, schizophrenia, sleep disorders, eating disorders, borderline personality disorder (and to a lesser extent other personality disorders), panic disorder, ADHD, epilepsy, Autism/Asperger's, sleep disorders, and potentially various substance abuse and dependence disorders. It would be evident to one skilled in the art that the determination in respect of EEG biomarkers may be performed in conjunction with statistics/data of a demographic associated with the user, along with self-report information, scores on various cognitive/emotional tasks, and biomarkers of types other than EEG (e.g. EMG, EOG, ECG, etc.).

As discussed supra multiple classification methods and algorithms may be applied to biosignals obtained for a user including, but not limited to, K-nearest neighbour algorithms, K-means algorithms, support vector machines, support vector networks, relevance vector machines, relevance vector networks, multilayer perceptron neural networks, neural networks, single layer perceptron models, logistic regression, logistic classifiers, decision trees, Bayesian linear classifiers, naïve Bayes, fuzzy entropy, fuzzy logic, linear discriminant analysis, linear regression, signal space projections, hidden Markov models, and ensemble classifiers including but not limited to bagging, random forests, random subspaces, bootstrapping aggregating, and AdaBoost.M1. Such classification algorithms may be applied to raw EEG data, filtered EEG data, and pre-processed EEG waveform data, including but not limited to EEG data that has been split into spectral components/Discrete Fourier transformed (FFT), split by waveform complexity ("fractal dimension"), and/or synchronization/synchronicity/synchrony of EEG activity between disparate brain regions.

As discussed within embodiments of the invention biosensor data, e.g. EEG data, may be stored within remote storage. This concept entitled by the inventors as MyBrain™ provides for the online storage and analysis of brainwave data using online cloud storage, deeper remote analysis, and optionally social media based sharing of user EEG data/analysis. Applications using this technology can upload EEG data temporarily stored on a user's PED to MyBrain™ whenever the PED is connected to a network with sufficient battery life or is on charge. MyBrain™ allows this temporarily stored EEG data to be stored for a longer period of time or indefinitely as well as allowing deeper and more processor-intensive analyses on the data to be performed rather than the more limited analyses on their PED. Further, such analyses may be performed over extended time periods, data sets, algorithms, etc. as well as correlated with databases of analyses of other users or those with known medical and/or neurological conditions. Once generated, these deeper and intensive analyses may be transmitted back to the user's PED and/or another device for use by an application and/or machine. MyBrain™ also allows users to share certain aspects of their information over social media with friends or for a group to collaborate such as within a group meditation for example even when the users cannot be present as may be the norm.

Additionally, the inventors have established generalized development tools for therapeutic applications of portable EEG, a software development kit (SDK) called Amygdala™ geared towards these purposes. Amygdala™ provides functionality that eases the creation of EEG-based applications for a User Assembly, and includes tools that specifically aid development of software intended for medical purposes, and self-improvement in the initial configuration. Amygdala provides developers and potentially users to exploit MyBrain™ for the remote storage of EEG data, the inclusion of third-party algorithms for EEG analysis, and the automated integration of audiovisual and various graphical elements within EEG applications. The inventors have exploited Amygdala™ and MyBrain™ in establishing EEG applications for a User Assembly, e.g. Neurosky™ Mindwave™ headset, of which three use the Amygdala™ SDK, three use MyBrain™, and two use both. These applications include two neurofeedback-based video games and two self-improvement applications, one based upon mindfulness meditation practice which is a well-established therapy for ADHD of all three subtypes, namely inattentive subtype, hyperactive subtype, and combined subtype, depression, anxiety, post-traumatic stress disorder, etc., and the other is based on an inventor established unique research-backed personality profiling method. These applications include "Upcake", "Upcake 2", "Psych Showdown" and "Transcend."

Transcend™ is a mobile application intended improve a user's ability to meditate, mindfulness meditation which is a core component of numerous neurofeedback exercises. The program works via the unique aforementioned meditation calculation method to detect a user's current meditation quality using their EEG data. Users meditate in "sessions" of a length they select, during which their meditation quality is recorded. During a session, a visual indicator is displayed onscreen that varies in accordance with their progress providing immediate feedback (neurofeedback). Following each session, users are shown what their average meditation quality was during the session. A session can either be done silently, or with voice guidance and advice, such that it essentially helps users through a variety of techniques for focusing attention on a single stimulus or action while tuning all others out—for example, focusing on one's breathing or repeating a single phrase over and over in one's head. Users are also able to view their average meditation quality over time, by viewing their previous session scores on a graph—thus allowing them to keep track of their progress.

Transcend™ interfaces with smartphones allowing users to practice EEG-guided meditation anytime and anywhere, which is a useful tool for improving one's meditation skill/meditation quality that can be applied in the practice of numerous subtypes of meditation (e.g. mindfulness meditation, transcendental meditation, etc.). It is also important for research purposes, as a meditation application tied solely to a stationary device, e.g. a FED, gives a sample of brain activity from only a single time of day and location under essentially controlled conditions. Further circadian rhythms and settings have a large impact on brain activity, such that since most people work from mid-morning to later afternoon, most readings would thus come from early evening and early morning, whilst a PED allows for use at any time with varying environments.

Transcend™ also adds an online component, allowing users to share their meditation information with other mindfulness practitioners. Furthermore, having a dedicated server (cloud) perform analyses on the data allows for the generation of more complex metrics using algorithms too processor-intensive (and thus battery-unfriendly) for use on a smartphone (or PED in general). It also allows for the storage of a virtually unlimited quantity of their EEG data safely and indefinitely. Additionally, Transcend™ takes information from users beyond the simple meditation readings, such as the date and time of each meditation session. Information about a user's context is essential for accurate interpretation of EEG data and accordingly, future embodiments of Transcend™ will merge the forms of data currently recorded (such as EEG data) with additional automatically acquired information through the PED such as ambient noise (by turning on and sampling the microphone during the meditation when the user would typically be silent), location using Global Positioning System (GPS), date/time information, and user information. Furthermore, a research-specific embodiment of Transcend exists that is solely designed for gathering data on users' meditation quality and associated metrics as mentioned supra (e.g. date and time of meditation session). Also, Transcend™ encourages its continued use by offering achievements/awards to users who improve their meditation abilities in ways detectable by the software.

Figure 13:
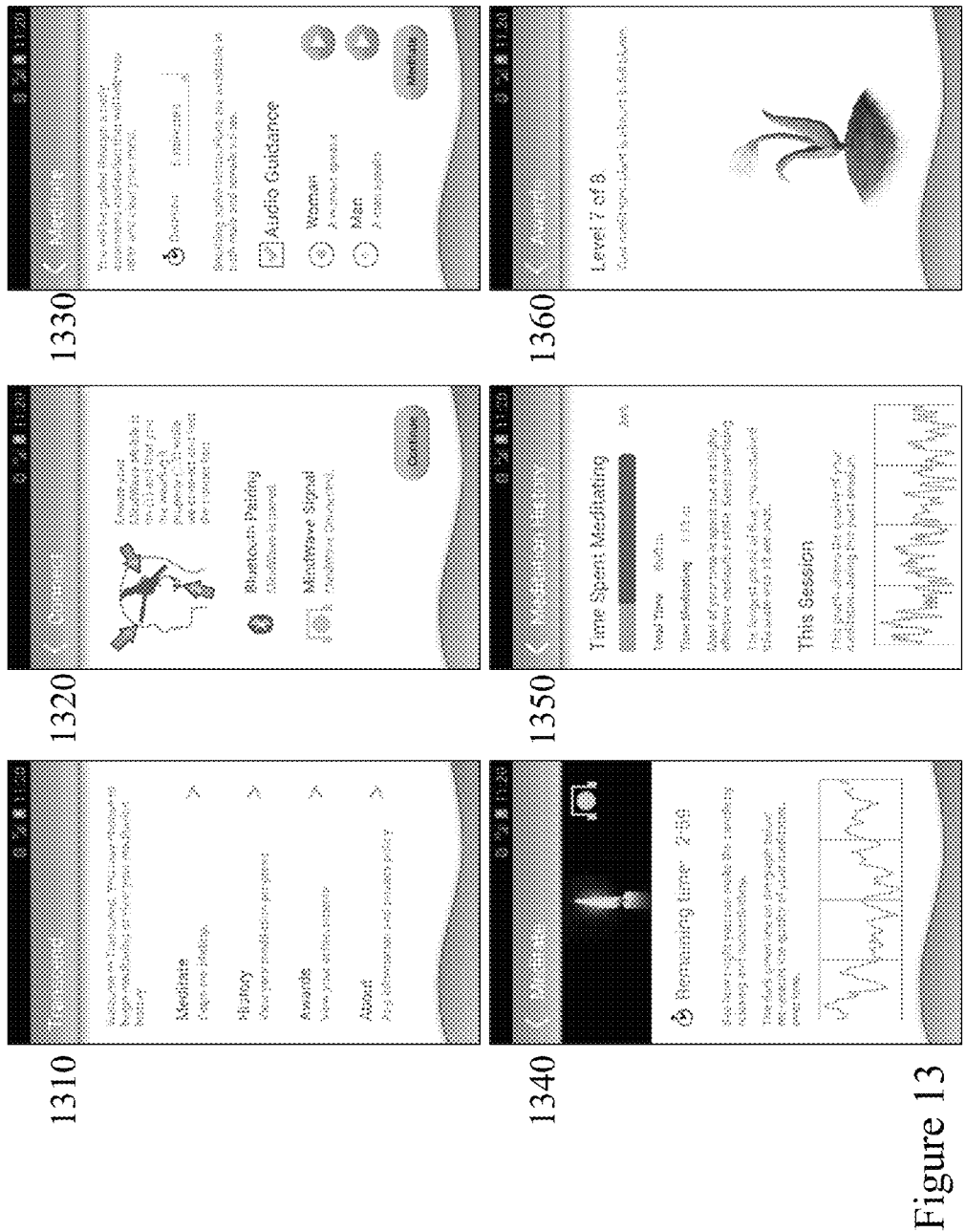
FIG. 13 depicts exemplary screenshots for Transcend™ implemented using a software development kit exploiting techniques and devices according to an embodiment of the invention.

Referring to FIG. 13 there are depicted first to sixth exemplary screenshots of Transcend™ wherein:

first screenshot 1310 depicts a user menu screen allowing them to begin meditating, view their progress via historical data, view their achievements, and obtain information about Transcend™;

second screenshot 1320 represents a user screen depicting connection of the user's EEG headset to their electronic device;

third screenshot 1330 represents a meditation screen for a user wherein the user can establish the duration of the meditation session as well as selecting whether they wish to have audio guidance, and if so whether it is a male or female voice;

fourth screenshot 1340 depicts a meditation screen for a user during a meditation session wherein the time remaining and their mental state progress are depicted;

fifth screenshot 1350 depicts a meditation screen for a user showing their meditation history indicating time meditating, total time, progress in last meditation session, and their maximum sustained meditation period; and sixth screen shot 1360 depicts a progress screen for a user.

Figure 14:
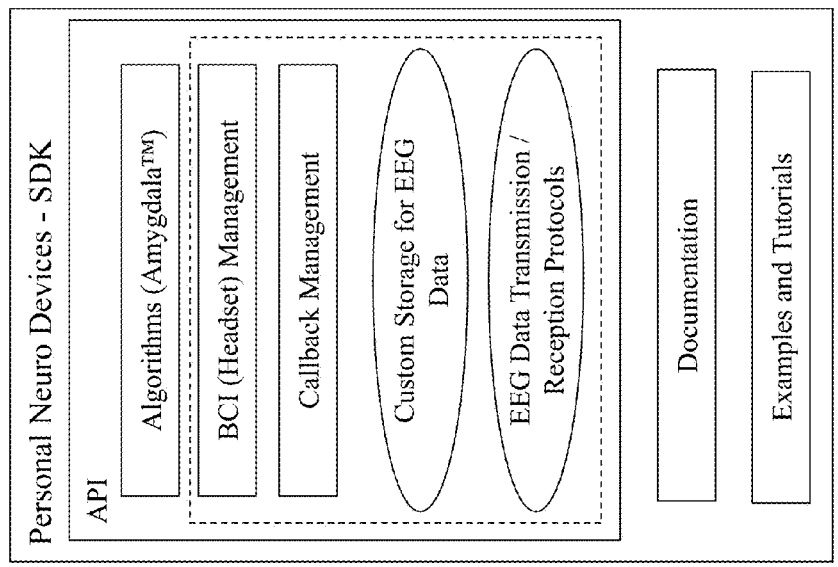
FIG. 14 depicts an exemplary layout for a software development kit exploiting techniques and devices according to an embodiment of the invention.

With respect to the software development kit (SDK) then this represents a collection of libraries (with accompanying documentation and examples) that are designed to simplify the development of neuro-based applications. Originally implemented for the Android platform the SDK may be ported to other platforms including, but not limited to, iOS, Windows, Blackberry, etc. Also, initially supporting the Neurosky Mindwave Mobile and Personal Neuro Devices headsets library extensions will allow the SDK to support a wide variety of different portable EEG headsets for use with a common application or development of platform specific applications. Referring to FIG. 14 the high level design of the Personal Neuro Devices (PND) SDK is depicted as comprising API, Documentation, and Examples/Tutorials. The rectangular shaped elements in the API indicate parts that are required whilst the oval shaped elements indicate parts that are optional or which might be implemented at a later date. The dashed rectangle around the BCI, Callback, Custom Storage, and Send EEG modules highlights the separation between the algorithms and the rest of the API. Accordingly, the SDK comprises essentially two independent libraries, one which is purely algorithms, and one that provides a standard interface to an EEG headset. Developers will therefore be able to include either library, or both, depending on their needs.

Algorithms (Amygdala™) is the module that contains all neuro based algorithms. Accordingly, these can contain any algorithm from mood (happy, sad, etc.) detection, to seizure detection, for example. Algorithms may be further grouped into subcategories. A requirement for the algorithms module is that it should work independently of other modules so that a developer can use PND algorithms without having to import the rest of our API BCI (Headset) Management handles connecting to and disconnecting from the headset, state recognition (i.e. in which state is the headset currently in? is it connecting, connected, disconnecting, disconnected, not found, etc.), and feature availability. In addition to handling state change related events, the headset module will also manage EEG related events, for example any new attention value being detected or a possible oncoming seizure.

Some exported applications from the PND SDK may through functionality to pick and choose which events need to be detected offer variable configurations for a headset supporting for example, multiple subscriber levels, upgrades, etc. In some embodiments of the invention the SDK may enable one of a plurality of applications within a PED for example such that a reduced functionality application may be exploited to lighten the load on the processor and prolong battery life when the battery within a PED reaches a predetermined threshold. The BCI Management offers a simple, standard way for the developer to connect to a headset which includes required preliminary steps (e.g. the connect method could include a check for Bluetooth connectivity)

Callback Management module allows the developer to attach various callback handlers to specified events. Handlers can be easily registered or unregistered from a specified event. When the specified event happens, all handlers registered to that event are executed (i.e. the system supports multiple handlers for each event).

Custom Storage for EEG data supports data structures for EEG data which are compatible with all or subsets of EEG headsets. Where possible a single data structure would allow the developer to save or retrieve EEG data without having to know the specifics of the current headset being used.

EEG Data Transmission/Reception Protocols provides for simplified upload/download of EEG to a server or servers. For example, this may be the PND server for data archiving, analysis etc. or the developer's server of choice.

Documentation (API Reference) describes the use and purpose of every publicly accessible class, method, parameter, and field.

Examples and Tutorials will help and encourage developers to use the PND API/SDK.

Considering the custom storage for EEG data wherein different storage structure versus a unified structure may be addressed within the API allowing a data structure to work seamlessly across different headsets. This may be achieved through the lowest common denominator/data conversion. In some cases, some sort of data conversion might simply mean reorganizing data in a certain way, while in others cases it might mean a loss of data (e.g. one headset returns raw data at 512 Hz while another returns data at 1024 Hz, then potentially the API may simply ignore each other data point from the second headset so that regardless of the headset used, the effective sample rate is always 512 Hz). Alternatively the 512 Hz data may be interpolated/replicated to simulate a 1024 Hz stream. Whether the loss or addition of data is significant will mostly depend on the algorithm(s) employed and the information to be extracted from the data. Whilst a unified data structure would also ease third party analysis and characterization plus integration with medical databases etc. this may provide a limitation depending on how the various headsets differ.

In some instances, some algorithms may not be supported on certain headsets either because they require proprietary data (e.g. Neurosky Attention/Relaxation), or the sampling rate is too low or the number of electrodes is insufficient, or the location of the electrode might not allow the headset to gather the required data. These are just some of the different ways that a headset's design might affect whether a certain algorithm can be used with a specific headset or not. As such, the SDK will include mechanisms to identify the requirements for each algorithm, e.g. this algorithm requires raw data sampled at a minimum of 200 Hz, with a minimum 8 bit resolution), or alternatively, each headset could be "aware" of which algorithms it is capable of using. In the case of proprietary data it may also be possible to develop functionally compatible custom implementations based on raw data.

Extending the MyBrain™ and Amygdala™ SDK the inventors are establishing "Introspect" a portable electronic device based consumer EEG software application which monitors and improves mental health. "Introspect" is intended to provide users with a multipurpose software bundle that provides users with a series of EEG-derived numerical metrics, e.g. mood rating, which allows the user to track multiple aspects of their brain health. The application then uses scores on these metrics to recommend specific built-in neurofeedback-based exercises intended to improve areas of weakness. Optionally, "Introspect" may also acquire non-built-in neurofeedback based exercises as the user progresses or particular characteristics of their advancement are identified. The derived results may be reported to users in the form of visual elements such as graphs that show progress in specific areas over time, which will be displayed on a dashboard-type Graphical User Interface (GUI). Areas of interest can be selected by users for inclusion on the dashboard, to avoid displaying unnecessary information, e.g. only epileptics would be interested in seizure data, although the epilepsy algorithm may still be executed to detect events which may indicate an onset or minor occurrences Certain iterations of Introspect will also include cognitive "brain training" tasks intended to help users improve on a variety of mental skills/characteristics traits such as working memory and attention. These tasks will augment the built-in neurofeedback exercises that are also intended to improve these features—thus providing another avenue through which users can improve themselves on their mental characteristics of choice. Furthermore, cognitive tasks augmented by neurofeedback in a variety of ways—and neurofeedback augmented by cognitive tasks—are also aspects of "Introspect." This includes but is not limited to: 1) the recommendation of a cognitive task/mental activity or cognitive tasks/mental activities as methods for users to increase or decrease the amplitude of certain EEG wavebands; 2) sessions in which users concurrently perform a neurofeedback exercise and a cognitive task, and are scored on both—i.e. a conglomerate measure of the quality of the session is generated; 3) testing the efficacy of a neurofeedback session by the performance of a cognitive task directly prior and following a neurofeedback exercise; and/or 4) testing the efficacy of a cognitive task in changing user EEG band activity by having users perform a neurofeedback exercise directly prior and following a cognitive task—thus allowing the software to alter which exercises are recommended to the user in response to the prior impact various exercises have had on user mental state/EEG activity.

The portability of the User Assembly, e.g. headset and software will allow users to take readings 24/7/365 (i.e. continuously). In certain embodiments the headset will be wearable continuously, thus allowing continuous scanning, whilst other embodiments will use experience sampling methods wherein users are reminded (if they activate the option), to perform scans at various intervals throughout the day. This will help prevent all readings from being taken in the same states of mind (e.g. states in which users are self-motivated enough to use the software), and/or at the same general times of day, e.g. before and after work. Avoiding these issues will allow Introspect to collect data that is much more representative of the user's day-to-day mental life—IE data that is much more meaningful and thus useful—to users and potentially various clinicians and medical professionals that may also refer to the recorded EEG data. "Introspect" includes self-report measures, for example 1-to-4 item (or perhaps more if allowed by the user) questionnaires presented randomly throughout the day, at requested intervals, and/or when users choose to fill them out. This information is then used in tandem with the EEG readings to generate more comprehensive data and more accurate results. Further, "Introspect" can be paired with other devices and/or systems such as the Nintendo™ Wii™ to compliment in the treatment for certain illnesses or overall physiological and psychological condition of the user. In the case of associating "Transcend" or other applications exploiting embodiments of the invention together with MyBrain™ and Amygdala™ SDK Wii then these can help with diseases related to poor physical fitness like heart disease and obesity as well as providing extra therapies for neurological and psychological conditions to associate with the physical remedies.

"Introspect" establishes algorithm-derived metrics for several neurological and psychological conditions including for example mood, concentration, stress, anxiety, cognitive functioning, stroke, and seizure detection.

Mood: for example an algorithm may calculate a simple numeric representation of the user's mood on an emotional valence (pleasant vs. unpleasant) scale going from 1 to 7 for example, where 1 is an extremely negative mood, and 7 extremely positive, see for example Schupp et al in "Affective Picture Processing as a Function of Preceding Picture Valence: An ERP Analysis" (Biol. Psychol., Vol. 91, pp 81-87).

Concentration: Algorithms for detecting this already exist in EEG based APIs for some headsets, e.g. Neurosky™ MindWave™. However, enhanced concentration metrics will include tracking other user activities such as one or more of speech, movement, blinking etc. via their PED and the EEG data. The rate of blinking has been shown to correlate strongly with attention level and is easily detectable with EEG, see for example Smilek et al in "Out of Mind, Out of Sight: Eye Blinking as Indicator and Embodiment of Mind Wandering" (Psychol. Sci., Vol. 21, pp 786-789).

Stress: This may be established upon a modification to a meditation metric of the inventors included in the Amygdala™ SDK. Furthermore, stress readings are roughly analogous to the inverse of relaxation, with several other factors taken into account. Including information of the "sweat potential", a large waveform generated when any moisture appears on the skin under the EEG electrode, will provide a second EEG feature that can be used to calculate stress levels given that sweating and stress are so closely linked.

Anxiety: A combination of self-report and EEG data on emotional valence, sweat potentials, and stress may be employed to provide an estimate of anxiety levels. However, the inventors are establishing sophisticated algorithms based upon identification of active regions. Specific sub-regions of the brain at the front of the head called the prefrontal cortex have descending inhibitory pathways into regions of the limbic system, the brain's emotion structures, involved in anxiety. Accordingly, waveforms indicative of activity in these regions can be established and inversely correlated with levels of anxiety.

Mental Clarity: This can be conceptualized as the speed and clarity of thought, ability to cognitively process, mental "sharpness," cognitive tempo, "acute intelligence," or inversely, level of confusion or mental "fogginess." Synchronized waveforms in separate areas of the brain can be analysed to provide a metric relating to cognitive functioning, especially in the gamma and beta bands. Research into this field includes Koenig et al in "Decreased EEG Synchronization in Alzheimer's Disease and Mild Cognitive Impairment" (Neurobiol. Aging, Vol. 26, pp 165-171).

Seizure Detection and Prediction: Whilst not necessarily useful for most users, epilepsy sufferers can use this metric to track the frequency and length of seizures, identify triggers, and provide early warnings for impending seizures. In the broader population rather than identifying the EEG activity which is significantly and distinctly changed by seizures, algorithms may be established that indicate early events not recognizable to the user necessarily or associated by the user to some other neurological, psychological, environmental, physical event. For epileptic customers many seizure-related features in EEG data can be mathematically extracted, of which some appear prior to the seizure. For well-established epileptic sufferers algorithms exist that can use these early features to predict upcoming seizures, with a very high degree of success, see for example Chisci et al in "Real-Time Epileptic Seizure Prediction Using AR Models and Support Vector Machines" (IEEE Trans. Biomed. Eng., Vol. 57, pp 1124-1132). The inventors note that such predictions can be used to alert medical personnel, family, friends, etc. as well as helping co-workers support an epileptic co-worker wherein the alert is communicated from the user's PED when the algorithm(s) detect the condition(s).

In a similar manner to Transcend™ and other applications developed exploiting embodiments of the invention the inventors have established MindMender™, a software suite for Android devices consisting of 3 EEG neurofeedback exercises intended to help treat certain symptoms resulting from traumatic brain injuries (TBI) and/or concussions, notably post-concussion syndrome. EEG data is recorded from the user via their EEG headset, which transmits the user's raw EEG data and some pre-calculated neurometrics (the user's attention and relaxation levels) to an Android PED. Other wavebands are extracted from the EEG data within our software via discrete Fourier transforms to calculate clarity. Whilst MindMender™ is not intended to directly repair physical damage produced by the initial injury, or cure the illness, it provides symptomatic treatment. Furthermore, it does not replace other treatments/more traditional forms of rehabilitation but rather it augments these therapies to potentially produce additional improvement, and provides patients with a therapy that can be continued once the medical system is no longer able to help.

To begin, users select a specific exercise based on improving one of three mental traits that tend to be deficient in TBI and concussion patients: attention, stress control, and "mental clarity". While performing each exercise, users are provided with a direct score from 1 to 100 in real-time for the metric said specific exercise is intended to improve. By altering their thinking or performing specific mental exercises, users are able to alter their mental state into that which the specific exercise aims for (e.g. an attentive state); with the numeric feedback informing the user of how successfully they're achieving that mental state. The techniques learned and used during the exercise allow the user to call up the desired state when needed (e.g. high attention) when not performing the exercise, by strengthening neural connections associated with said state. Included with each neurofeedback exercise is a series of methods for calling up the desired state: mental strategies, which are based on those used to increase the associated metrics. Also, feedback is given following each session on ways the user can improve their performance. Scores are tracked over time, so patients can monitor their progress on each of the 3 metrics.

Following a neurofeedback session (of any exercise), a total score is shown to the user, along with a chart showing how their brain activity went up and down throughout the session. Advice for improvement is also provided. Users are therefore able to see their progress over time on each exercise on a series of charts. Scores for all previous exercise sessions are included, so users can see their improvement. This will provide users with motivation to continue, i.e. a gamification element, and help them understand the kinds of functional improvements they should be seeing in day-to-day life. It also introduces a placebo element as while the exercises are effective on their own, any intervention is more effective if users know they're receiving it.

Within embodiments of the invention described supra in respect of FIGS. 1 through 12 the signal processing and analysis of raw EEG data acquired from an EEG sensor or sensors has been described and presented as being performed on a PED/FED associated with the user with further analysis being performed on a remote server system. It would be evident to one skilled in the art that the analysis of EEG data relating to a user may be performed in some embodiments solely on the user's PED/FED, in other embodiments of the invention this processing may be solely on the remote server system, and in others distributed between the user's PED/FED and the remote server system. In other embodiments of the invention initial processing or pre-processing of the EEG data may be performed at the user's PED/FED and then more detailed analysis and post-processing applied at the remote server. In other embodiments of the invention initial processing may be performed upon the current EEG data and/or an EEG data stored relating to a recent predetermined period of time whilst processing over a longer historical period of time is performed on the remote server that stores user EEG data historically. This historical backup of EEG data being performed for example by MyBrain™ as described supra.

Specific details are given in the above description to provide a thorough understanding of the embodiments. However, it is understood that the embodiments may be practiced without these specific details. For example, circuits may be shown in block diagrams in order not to obscure the embodiments in unnecessary detail. In other instances, well-known circuits, processes, algorithms, structures, and techniques may be shown without unnecessary detail in order to avoid obscuring the embodiments.

Implementation of the techniques, blocks, steps and means described above may be done in various ways. For example, these techniques, blocks, steps and means may be implemented in hardware, software, or a combination thereof. For a hardware implementation, the processing units may be implemented within one or more application specific integrated circuits (ASICs), digital signal processors (DSPs), digital signal processing devices (DSPDs), Programmable Logic Devices (PLDs), field programmable gate arrays (FPGAs), processors, controllers, micro-controllers, microprocessors, other electronic units designed to perform the functions described above and/or a combination thereof.

Also, it is noted that the embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be rearranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Furthermore, embodiments may be implemented by hardware, software, scripting languages, firmware, middleware, microcode, hardware description languages and/or any combination thereof. When implemented in software, firmware, middleware, scripting language and/or microcode, the program code or code segments to perform the necessary tasks may be stored in a machine readable medium, such as a storage medium. A code segment or machine-executable instruction may represent a procedure, a function, a subprogram, a program, a routine, a subroutine, a module, a software package, a script, a class, or any combination of instructions, data structures and/or program statements. A code segment may be coupled to another code segment or a hardware circuit by passing and/or receiving information, data, arguments, parameters and/or memory contents. Information, arguments, parameters, data, etc. may be passed, forwarded, or transmitted via any suitable means including memory sharing, message passing, token passing, network transmission, etc.

For a firmware and/or software implementation, the methodologies may be implemented with modules (e.g., procedures, functions, and so on) that perform the functions described herein. Any machine-readable medium tangibly embodying instructions may be used in implementing the methodologies described herein. For example, software codes may be stored in a memory. Memory may be implemented within the processor or external to the processor and may vary in implementation where the memory is employed in storing software codes for subsequent execution to that when the memory is employed in executing the software codes. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" may represent one or more devices for storing data, including read only memory (ROM), random access memory (RAM), magnetic RAM, core memory, magnetic disk storage mediums, optical storage mediums, flash memory devices and/or other machine readable mediums for storing information. The term "machine-readable medium"

includes, but is not limited to portable or fixed storage devices, optical storage devices, wireless channels and/or various other mediums capable of storing, containing or carrying instruction(s) and/or data.

The methodologies described herein are, in one or more embodiments, performable by a machine which includes one or more processors that accept code segments containing instructions. For any of the methods described herein, when the instructions are executed by the machine, the machine performs the method. Any machine capable of executing a set of instructions (sequential or otherwise) that specify actions to be taken by that machine are included. Thus, a typical machine may be exemplified by a typical processing system that includes one or more processors. Each processor may include one or more of a CPU, a graphics-processing unit, and a programmable DSP unit. The processing system further may include a memory subsystem including main RAM and/or a static RAM, and/or ROM. A bus subsystem may be included for communicating between the components. If the processing system requires a display, such a display may be included, e.g., a liquid crystal display (LCD). If manual data entry is required, the processing system also includes an input device such as one or more of an alphanumeric input unit such as a keyboard, a pointing control device such as a mouse, and so forth.

The memory includes machine-readable code segments (e.g. software or software code) including instructions for performing, when executed by the processing system, one of more of the methods described herein. The software may reside entirely in the memory, or may also reside, completely or at least partially, within the RAM and/or within the processor during execution thereof by the computer system. Thus, the memory and the processor also constitute a system comprising machine-readable code.

In alternative embodiments, the machine operates as a standalone device or may be connected, e.g., networked to other machines, in a networked deployment, the machine may operate in the capacity of a server or a client machine in server-client network environment, or as a peer machine in a peer-to-peer or distributed network environment. The machine may be, for example, a computer, a server, a cluster of servers, a cluster of computers, a web appliance, a distributed computing environment, a cloud computing environment, or any machine capable of executing a set of instructions (sequential or otherwise) that specify actions to be taken by that machine. The term "machine" may also be taken to include any collection of machines that individually or jointly execute a set (or multiple sets) of instructions to perform any one or more of the methodologies discussed herein.

The foregoing disclosure of the exemplary embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A device comprising:
   a back to fit around only a predetermined portion of the rear of a user's head;
   a pair of arms formed from a first flexible material connected to the back and projecting forward to fit along the sides of the user's head;
   a pair of support guides, each coupled to an arm, formed from a second flexible material and projecting forward to fit over a temple region of the user;
   a pair of first electroencephalography (EEG) sensors, each first EEG sensor configured to engage a temple of the user and forming a tip portion of its respective support guide distal to an end of the support guide joining its respective arm;
   a pair of second EEG sensors disposed within the back to engage the occipital region of the user's head, wherein
   at least one of the pair of arms and the pair of support guides are configured to apply pressure against at least the sides and temples respectively of the user's head in order to retain the device in position on the user's head absent any other retention means.

2. The device according to claim 1, wherein
   for a user's head within a predetermined range of dimensions:
   the pair of arms and pair of support guides are dimensioned such that the first EEG sensors are configured to be positioned proximate nodes O1 and O2 according to the conventional labelling of nodes of the brain; and
   the second EEG sensors are configured to be positioned proximate nodes F3 and F4 according to the conventional labelling of nodes of the brain.

3. The device according to claim 1, further comprising:
   a wireless transmitter operating according to a predetermined standard to transmit at least one of raw EEG data and processed EEG data from the pairs of first and second EEG sensors to another device.

4. The device according to claim 1, further comprising:
   a wireless receiver operating according to a first predetermined standard to receive EEG data from an EEG sensor forming part of a head mounted display adapted to be mounted on the user's head; and
   a wireless transmitter operating according to a second predetermined standard to transmit the received EEG sensor data to another device.

5. The device according to claim 1, wherein
   at least one of the arms and the support guides are essentially arcuate from a first end configured to be towards the rear of the user's head to a second distal end configured to be towards the front of the user's head; and
   at least one of the arms and the support guides have a spacing configured to be laterally smaller than the lateral dimensions of user's heads within a predetermined range of dimensions.

6. The device according to claim 1, wherein
at least one arm of the pair of arms comprises an additional EEG sensor disposed at a predetermined position along the arm.

7. The device according to claim 1, wherein
at least one support guide of the pair of support guides comprises an additional EEG sensor disposed at a predetermined position along the at least one support guide of the pair of support guides.

8. The device according to claim 1, wherein
the pair of arms are designed in conjunction with the back such that a predetermined portion of each arm of the pair of arms configured to engage the upper region of the user's ears either directly or via a frame of a pair of eyeglasses worn by the user.

9. The device according to claim 1, further comprising
a third EEG sensor attached to an arm of the pair of arms and configured to be positioned proximate a node according to the conventional labelling of nodes of the brain selected from the group comprising T5, T3, T4 and T6.

10. The device according to claim 1, wherein
the back, pair of arms, and pair of support guides form a predetermined portion of a head mounting for a wearable item, the wearable item is selected from the group comprising prescription eyeglasses, safety eyeglasses, a head mounted display, an immersive head mounted display, a protective helmet, a sports helmet, a bicycle helmet, a pair of headphones, an application specific headset, a headset, and a headband.

11. The device according to claim 1, further comprising
a microprocessor applying at least one algorithm of a plurality of algorithms to EEG data received from at least one of the pair of first EEG sensors and the pair of second EEG sensors, wherein the algorithm comprises applying at least one of a signal processing algorithm and a classification algorithm upon the EEG data.

12. The device according to claim 1, further comprising
a microprocessor applying at least one algorithm of a plurality of algorithms to EEG data received from at least one of the pair of first EEG sensors and the pair of second EEG sensors to generate processed EEG data and applying another algorithm of the plurality of algorithms to the processed EEG data and user data;
a wireless receiver forming part of the back of the device operating according to a predetermined standard for acquiring the user data relating to at least one of an activity and a context of the user from another electronic device associated with the user.

13. A device comprising:
a housing to fit around only a predetermined portion of the back of a user's head;
a pair of arms formed from a first flexible material connected to the housing projecting forward to fit along the sides of the user's head;
a pair of support guides each coupled to an arm of the pair of arms, formed from a second flexible material, projecting forward to fit over a temple region of the user and including a first electroencephalography (EEG) sensor;
a pair of second EEG sensors disposed within the housing configured to engage the occipital region of the user's head;
a microprocessor applying at least one algorithm of a plurality of algorithms to EEG data obtained from the pair of first EEG sensors and the pair of second EEG sensors to generate processed EEG data; and
a wireless transceiver operating according to a first predetermined standard to transmit processed EEG data to another device and acquire data relating to activities of a user of the device, wherein
at least one the pair of arms and pair of support guides are configured to apply pressure against at least the sides and temples respectively of the user's head in order to retain the device in position on the user's head absent any other retention means.

14. A device according to claim 13, wherein
the algorithm of the plurality of algorithms generates a determination of a state of a user of the device in dependence upon the processed EEG data, data relating to an activity of the user, and data relating to a context of the user.

15. A device according to claim 13, wherein
the algorithm of the plurality of algorithms processes stored processed EEG data in dependence upon at least one of an EEG footprint of a plurality of EEG footprints, a biomarker of a plurality of biomarkers, and statistical data relating to a demographic associated with the user; wherein
the algorithm of the plurality of algorithms is established in dependence upon at least one of data relating to an activity of the user and data relating to a context of the user.

16. A device according to claim 15, wherein
the algorithm of the plurality of algorithms determines a state of the user and an indicator relating to the determined state; wherein
the state for which a determination is made is selected from the group comprising stress, relaxation, concentration, meditation, an emotion, a mood, anxiety, drowsiness, and sleep; and
the indicator relating to the determined state is associated with at least one of a valence of the state, intensity of state, dominance of the state, and cognitive functioning of the user.

17. The device according to claim 13, wherein
the housing, pair of arms, and pair of support guides form a predetermined portion of a head mounting for a wearable item, the wearable item is selected from the group comprising prescription eyeglasses, safety eyeglasses, a head mounted display, an immersive head mounted display, a protective helmet, a sports helmet, a bicycle helmet, a pair of headphones, an application specific headset, a headset, and a headband.

18. A device comprising:
a frame for mounting to a user's head which can be linked to one or more wearable items providing the user with a predetermined functionality, the frame comprising
a housing to fit around only a predetermined portion of the back of a user's head;
a pair of arms formed from a first flexible material connected to the housing projecting forward to fit along the sides of the user's head;
a pair of support guides each coupled to an arm of the pair of arms, formed from a second flexible material, projecting forward to fit over a temple region of the user and including a first electroencephalography (EEG) sensor;
a pair of second EEG sensors disposed within the housing configured to engage the occipital region of the user's head;

a microprocessor applying at least one algorithm of a plurality of algorithms to EEG data obtained from the pair of first EEG sensors and the pair of second EEG sensors to generate processed EEG data; and a wireless transceiver operating according to a first predetermined standard to transmit the processed EEG data to another device and acquire data relating to activities of a user of the device.

19. The device according to claim 18, wherein the wearable item is selected from the group comprising prescription eyeglasses, safety eyeglasses, a visor, a head mounted display, an immersive head mounted display, a protective helmet, a sports helmet, a bicycle helmet, a pair of headphones, an application specific headset, and a telephone headset.

* * * * *